(12) United States Patent
Yang

(10) Patent No.: US 6,825,236 B2
(45) Date of Patent: Nov. 30, 2004

(54) COLCHICINE DERIVATIVES

(75) Inventor: Li-Xi Yang, San Francisco, CA (US)

(73) Assignees: California Pacific Medical Center, San Francisco, CA (US); Catholic Healthcare West, San Francisco, CA (US)

(*) Notice: Subject to any disclaimer, the term of this patent is extended or adjusted under 35 U.S.C. 154(b) by 0 days.

(21) Appl. No.: 10/414,076

(22) Filed: Apr. 14, 2003

(65) Prior Publication Data
US 2004/0204370 A1 Oct. 14, 2004

(51) Int. Cl.[7] ...................... A61K 31/165; C07C 233/00
(52) U.S. Cl. ....................... 514/617; 514/618; 514/619; 564/182; 564/162; 564/163; 536/1.11; 536/4.1
(58) Field of Search ................................. 564/202, 427, 564/182, 162, 163; 514/427, 467, 25, 618, 619, 617, 534, 625; 549/452, 417; 560/1.11, 4.1, 250, 217

(56) References Cited

U.S. PATENT DOCUMENTS

| 5,220,002 A | * 6/1993 | Akiyama ..................... 536/18.7 |
| 5,777,136 A | 7/1998 | Bombardelli |
| 5,973,204 A | 10/1999 | Bombardelli |
| 6,080,739 A | 6/2000 | Bombardelli |

FOREIGN PATENT DOCUMENTS

| WO | WO 91/02084 | * 2/1991 | ............ C12Q/1/02 |
| WO | WO 01/68597 | * 9/2001 | ......... C07C/323/41 |

OTHER PUBLICATIONS

The American Heritage Dictionary of the English Language, Third Edition, 1992.*
Sharma et al "Synthesis and Binding to Tubulin of Colchicine Spin Probes", J. Med. Chem. 1984, 27, 1729–1733.*
Guan et al "Antitumor Agents. Synthesis and Biological Evaluation of Tridemethylthiocolchicine Analogues as Novel Topoisomerase II Inhibitors", J. Med. Chem. 1998, 41, 1956–1961.*
Floyd et al "Photoafinity Labeling of Tubulin with (2–nitro–4–azidopheynyl)deacetylcolchicime: Direct evidence for two colchicine binding sites", Biochemistry, 1989, 28(21) 8515–8525.*
Sun, L., et al., 1993, "Antitumor Agents. 141. Synthesis and Biological Evaluation of Novel Thiocolchicine Analogs: N–Acyl–, N–Aroyl–, and N–(Substituted benzyl)deacetylthiocolchicimes as Potent Cytotoxic and Antimitotic Compounds", J. Med. Chem., 36:1474–1479.
Zang, S., et al., "Antitumor Agents. 196. Substituted 2–Thienyl–1,8–naphthyridin–4ones: their Synthesis, Cytotoxicity, and Inhibition of Tubulin Polymerization", J. Med. Chem., 42:4081–4087.

Brossi, A., et al., 1983, Biological Effects of Modified Colchicines. 2. Evalution of Catecholic Colchicines, Colchifolines, Colchicide, and Novel N—Acyl—and N—Aroyldeacetylcolchicines, J. Med. Chem., 26, 1365–1369.
De Vincenzo, R., et al., 1998, "Antiproliferative activity of colchicine analogues on MDR–positive and MDR–negative human cancer cell lines" Anti–Cancer Drug Design, 13:19–33.
Dumont, R., et al, 1987, "A Novel Synthesis of Colchicide and Analogues from Thiocolchicine and Congeners: Reevalution of Colchicide as a Potenial Antitumor Agent", J. Med Chem., 30:732–735.
Gelmi, M.L., et al., 1999, "N–Deacetyl–N–aminoacylthicolchicine Derivatives: Synthesis and Biological Evaluation on MDR–Positive and MDR–Negative Human Cancer Cell Lines", J. Med. Chem., 42:5272–5276.
Kerekes, P. et al. 1985, "Synthesis and Biological Effects of Novel Thiocolchicines. 3. Evaluation of N–Acyldeacetylthiocolchicines, N–(Alkoxycarbonyl)deacetylthiocolchicines, and O–Ethyldemethylthiocolchicines. New Synthesis of Thiodemecolcine and Antileukemic Effects of Demethyl–and 3–Demethylthiocolchicine", J. Med. Chem., 28:1204–1208.
Lin, T., et al., 1980, "Synthesis and Biological Activities of Chloroethylurea, Methylurea, and Nitrosourea Analogues of N–Deacetylmethylthiocolchicine", J. Med., Chem., 23:1440–1442.
Muzaffar, A., et al., 1990, "Antiubulin Effects of Derivatives of 3–Demethylthiocolchine, Methylthio Ethers of Natural Colchicinoids, and Thioketones Derived from Thiocolchicine. Comparison with Colchicinoids", 33:567–571.
Rösner, M., 1981, "Biological Effects of Modified Colchicines. Improved Preparation of 2–Demethylcolchicine, 3–Demethylcochicine, and (+)–Colchicine and Reassignment of the Position of the Double Bond in Dehydro–7 deacetamidocolchicines", J. Med. Chem., 24:257–261.

(List continued on next page.)

Primary Examiner—James O. Wilson
Assistant Examiner—Ganapathy Krishnan
(74) Attorney, Agent, or Firm—Cooley Godward LLP

(57) ABSTRACT

Certain N-deacetylcolchicine and N-deacetylthiocolchine derivatives are described wherein the 7-N position on the B ring is substituted with the group —C(O)—(CHR$_4$)$_m$—AR, wherein m is an integer of 0–10, A is S, O, N or a covalent bond; R$_1$ is substituted phenyl or substituted benzoyl; optionally substituted cycloalkyl of 3–7 carbons; optionally substituted naphtyl; an optionally substituted imide ring; an optionally substituted 5 or 6 member heterocycle with at least one N, S, or O in the ring; or an optionally substituted fused heterocyclic or fused carboxyclic ring system; R$_2$ (at the 2-position of the A ring) is methoxy, hydroxy, or methylenedioxy when taken together with R$_3$; R$_3$ (at the 3-position of the A ring) is methoxy, hydroxy, a monosaccharide radical, or is methylenedioxy when taken together with R$_2$; and R$_4$ is H or is H or methyl when m is 1. Also dimers of such compounds are disclosed. When combined with suitable pharmaceutical excipients, these compounds are useful for treating various types of cancer.

49 Claims, No Drawings

OTHER PUBLICATIONS

Shi, Q., et al., 1997, "Antituor Agents. 172, Synthesis and Biological Evaluation of Novel Deacetamidothicolchicin–7 ols and Ester Analogs as Antitubulin Agents", *J. Med. Chem.*, 40:961–966.

Shiau, G.T., et al., 1975, "Alkylthiocolchicines and N–Deacetyl–alkylthiocolchicines and Their Antileukemic Activity", *J. Pharm. Sci.*, 4:646–648.

Shiau, G.T., et al., 1978, "Synthesis and Evaluation of N–Deacetyl–N–glycosylalklthiocolchicines as Antileukemic Agents", *J. Pharm. Sci.*, 67:394–397.

Sun, L., et al., 1993, "Antitumor Agents. 139. Synthesis and Biological Evaluation of Thiocochicine Analogs 5,6–Dihydro–6(S)–(acyloxy)–and 5,6–Dihydro–6(S)–[aroyloxy)methyl]–1,2,3,– trimethoxy–9–(methylthio)–8H–cyclohepta[a] naphthalene–8–ones as Novel Cytotoxic and Antimitioic Agents", *J. Med. Chem.*, 36:544–551.

* cited by examiner

COLCHICINE DERIVATIVES

GOVERNMENT FUNDING

Work for this invention was funded at least in part by a grant from Department of Defense, U.S. Medical and Materiel Command, Grant number 3106-01-00.

INTRODUCTION

1. Field of the Invention

This invention relates to novel colchicine derivatives that are useful for treating various types of cancer.

2. Background of the Invention

Colchicine is a known compound having the following formula

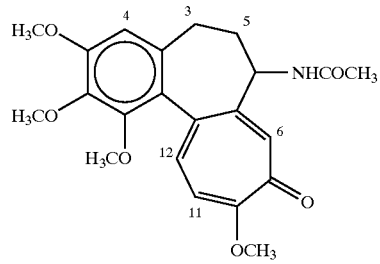

The rings are referred to as A (the phenyl ring showing methoxygroups at 1, 2, and 3), B (7-membered ring with the amide group at 7), and C (the third ring). The compound has been used to treat gout and also exhibits antitumor activity.

The antitumor activity of colchicine, which is the major alkaloid of the autumn crocus, *Colchicum autumnale*, and the African climbing lily, *Gloriosa superba*, was first reported at the beginning of the 20$^{th}$ century. The elucidation of its structure was finally completed from X-ray studies and a number of total syntheses (see Shiau et al. J. Pharm. Sci. 1978, 67(3) 394–397). Colchicine is thought to be a mitotic poison, particularly in tyhmic, intestinal, and hermatopoietic cells, which acts as a spindle poison and blocks the kinesis. Its effect on the mitotic spindle is thought to represent a special case of its effects on various organized, labile, fibrillar systems concerned with structure and movement.

Thiocolchicine is a compound of the above formula, wherein the 10-methoxy group is replaced by a 10-methylthio group. The removal of the acetyl group from the 7-position results in N-deacetylcolchicine or N-deactylthiocolchicine. We have now discovered new derivatives of colchicine and thiocolchicine that exhibit useful anticancer activity.

SUMMARY OF THE INVENTION

One aspect of this invention is a compound represented by the formula

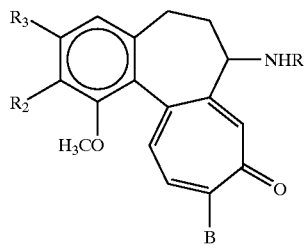

wherein

R is $C(O)-(CHR_4)_m-A-R_1$ where m is 1–10,

A is S, O, N or a covalent bond, $R_1$ is substituted phenyl or substituted benzoyl;

B is methoxy or methylthio;

$R_2$ is methoxy, hydroxy, or methylenedioxy when taken together with $R_3$;

$R_3$ is methoxy, hydroxy, a monosaccharide radical, or is methylenedioxy when taken together with $R_2$; and $R_4$ is H or is H or methyl when m is 1.

Another aspect of this invention is a compound represented by the formula

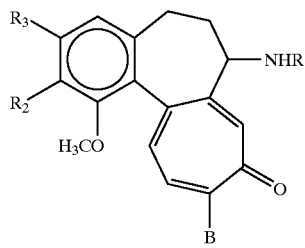

wherein

R is $C(O)-(CHR_4)_m-A-R_1$ where m is 0–10;

A is oxygen, sulfur, nitrogen, or a covalent bond;

$R_1$ is phenyl substituted with one to five substituents (the substituents being selected from halo, lower alkyl, cyano, nitro, amino, halogenated lower alkyl, carbonyl, hydroxycarbonyl, lower alkylcarbonyloxy, benzyloxy, optionally substituted 5 or 6 membered heterocyclic ring, an imide ring, lower alkoxycarbonyl, and lower alkylcarbonylamino, optionally substituted cycloalkyl of 3–7 carbons, optionally substituted naphtyl, an optionally substituted imide ring, an optionally substituted 5 or 6 member heterocycle (with at least one N, S, or O in the ring), or an optionally substituted fused heterocyclic or fused carboxyclic ring system;

B is methoxy or methylthio;

$R_2$ is methoxy, hydroxy, or methylenedioxy when taken together with $R_3$;

$R_3$ is methoxy, hydroxy, a monosaccharide radical, or is methylenedioxy when taken together with $R_2$; and $R_4$ is H or H or methyl when m is 1.

Another aspect of this invention is a compound represented by the formula

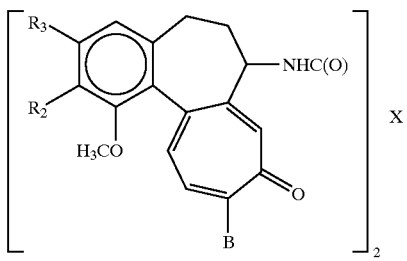

wherein

B is methoxy or methylthio;

R$_2$ is methoxy, hydroxy, or methylenedioxy when taken together with R$_3$;

R$_3$ is methoxy, hydroxy, a monosaccharide radical, or is methylenedioxy when taken together with R$_2$; and X is a linking group.

Another aspect of the invention is a pharmaceutical composition useful for treating cancer in a warm-blooded animal, which composition comprises compound of the invention as defined herein in combination with a pharmaceutically acceptable excipient.

Another aspect of this invention is a method for treating cancer in a warm-blooded animal, which method comprises administering a therapeutically effective amount of a compound of the invention as defined herein. The compound is administered in a therapeutically effective dose by appropriate administration, e.g. orally, topically, or parenterally.

Other aspects of this invention will be apparent to one of skill in the art by reviewing the ensuing specification.

DETAILED DESCRIPTION

Overview

In general the compounds of this invention can be viewed as derivatives of colchicine. The novel compounds of the invention are active against tumors in mice and are generally well tolerated. They are useful for treating various types of cancer and can be formulated to prepare pharmaceutical preparations, e.g. for oral, topical, or parenteral administration.

Definitions

The term "alkyl" refers to a monovalent, saturated aliphatic hydrocarbon radical having the indicated number of carbon atoms. For example, a "C1–6 alkyl" or an "alkyl of 1–6 carbons" or "Alk 1–6" would refer to any alkyl group containing one to six carbons in the structure. "C1–20 alkyl" refers to any alkyl group having one to twenty carbons. Alkyl may be a straight chain (i.e. linear) or a branched chain. Lower alkyl refers to an alkyl of 1–6 carbons. Representative examples lower alkyl radicals include methyl, ethyl, n-propyl, n-butyl, n-pentyl, n-hexyl, isopropyl, isobutyl, isopentyl, amyl, sec-butyl, tert-butyl, tert-pentyl and the like. Higher alkyl refers to alkyls of seven carbons and above. These include n-heptyl, n-octyl, n-nonyl, n-decyl, n-dodecyl, n-tetradecyl, n-hexadecyl, n-octadecyl, n-eicosyl, and the like, along with branched variations thereof. The radical may be optionally substituted with substituents at positions that do not significantly interfere with the preparation of compounds failing within the scope of this invention and that do not significantly reduce the efficacy of the compounds. The alkyl may be optionally substituted with one to five substituents independently selected from the group consisting of halo, lower alkoxy, hydroxy, cyano, nitro, or amino.

The term "alkoxy" refers to a monovalent radical of the formula RO—, where R is an alkyl as defined herein. Lower alkoxy refers to an alkoxy of 1–6 carbon atoms, with higher alkoxy is an alkoxy of seven or more carbon atoms. Representative lower alkoxy radicals include methoxy, ethoxy, n-propoxy, n-butoxy, n-pentyloxy, n-hexyloxy, isopropoxy, isobutoxy, isopentyloxy, amyloxy, sec-butoxy, tert-butoxy, tert-pentyloxy, and the like. Higher alkoxy radicals include those corresponding to the higher alkyl radicals set forth herein. The radical may be optionally substituted with substituents at positions that do not significantly interfere with the preparation of compounds falling within the scope of this invention and that do not significantly reduce the efficacy of the compounds. The radical may be optionally substituted with one to five substituents independently selected from the group consisting of halo, lower alkyl, lower alkoxy, hydroxy, cyano, nitro, or amino.

The term "cycloalkyl" refers to a monovalent, alicyclic, saturated hydrocarbon radical having three or more carbons forming the ring. While known cycloalkyl compounds may have up to 30 or more carbon atoms, generally there will be three to seven carbons in the ring. The latter include, for example, cyclopropyl, cyclobutyl, cyclopentyl, cyclohexyl, and cycloheptyl. The radical may be optionally substituted with substituents at positions that do not significantly interfere with the preparation of compounds falling within the scope of this invention and that do not significantly reduce the efficacy of the compounds. The cycloalkyl is optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

The term "hydroxycarbonyl" or "carboxy" is a monovalent radical having the formula —C(O)OH.

The term "lower alkoxycarbonyl" is a monovalent radical having the formula —C(O)OAlk, where Alk is lower alkyl.

The term "lower alkylcarbonyloxy" is a monovalent radical having the formula —OC(O)Alk, where Alk is lower alkyl.

The term "lower alkylcarbonylamino" is a monovalent radical having the formula —NHC(O)Alk, where Alk is lower alkyl.

A "halo" substitutent is a monovalent halogen radical chosen from chloro, bromo, iodo, and fluoro. A "halogenated" compound is one substituted with one or more halo sustituent.

A "phenyl" is a radical formed by removal of a hydrogen from a benzene ring. The phenyl is said to be "substituted" when substituted with from one to five substituents. These substituents are preferably independently selected from the group consisting of halo, lower alkyl, hydroxy, lower alkoxy, cyano, nitro, amino, halogenated lower alkyl, halogenated lower alkoxy, carbonyl, hydroxycarbonyl, lower alkylcarbonyloxy, benzyloxy, optionally substituted 5 or 6 membered heterocyclic ring, an imide ring, lower alkoxycarbonyl, and lower alkylcarbonylamino (where the alkyl is optionally substituted with a halo such as chloro).

A "carbamoyloxy" is a monovalent radical of the formula R$_{13}$R$_{14}$NC(O)O— (i.e. an aminocarbonyloxy) where R$_{13}$ and R$_{14}$ together form a cyclic amino with the nitrogen atom, or each of R$_{13}$ and R$_{14}$ is independently hydrogen, lower alkyl, hydroxy lower alkyl, hydroxy lower alkyl, amino lower alkyl, lower cycloalkyl, phenyl (substituted or unsubstituted), or benzyl (substituted or unsubstituted).

Examples include aminocarbonyloxy, methylaminocarbonyloxy, dimethyl aminocarbonyloxy, [4-(1-piperidino)-1-piperidino]carbonyloxy, 1-morpholinocarbonyloxy, 1-pyrrolidinyl, 1-piperazinecarbonyloxy, and others delineated herein.

A "5-membered heterocyclic ring" is a monovalent radical of a 5-member closed ring containing carbon and at least one other element, generally nitrogen, oxygen, or sulfur and may be fully saturated, partially saturated, or unsaturated (i.e. aromatic in nature). Generally the heterocycle will contain no more than two hetero atoms but may contain 3. Representative examples of unsaturated 5-membered heterocycles with only one hetero atom include 2- or 3-pyrrolyl, 2- or 3-furanyl, and 2- or 3-thiophenyl. Corresponding partially saturated or fully saturated radicals include 3-pyrrolin-2-yl, 2- or 3-pyrrolidinyl, 2- or 3-tetrahydrofuranyl, and 2- or 3-tetrahydrothiophenyl. Representative unsaturated 5-membered heterocyclic radicals having two hetero atoms include imidazolyl, oxazolyl, thiazolyl, pyrazolyl, and the like. The corresponding fully saturated and partially saturated radicals are also included. The heterocyclic radical is bonded through an available carbon atom in the heteocyclic ring. The radical may be optionally substituted with substituents at positions that do not significantly interfere with the preparation of compounds falling within the scope of this invention and that do not significantly reduce the efficacy of the compounds. The ring is optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

A "6-membered heterocyclic ring" is a monovalent radical of a 6-member closed ring containing carbon and at least one other element, generally nitrogen, oxygen, or sulfur and may be fully saturated, partially saturated, or unsaturated (i.e. aromatic in nature). Generally the heterocycle will contain no more than two hetero atoms. Representative examples of unsaturated 6-membered heterocycles with only one hetero atom include 2-, 3-, or 4-pyridinyl, 2H-pyranyl, and 4H-pryanyl. Corresponding partially saturated or fully saturated radicals include 2-, 3-, or 4-piperidinyl, 2-, 3-, or 4-tetrahydropyranyl and the like. Representative unsaturated 6-membered heterocyclic radicals having two hetero atoms include 3- or 4- pyridazinyl, 2-, 4-, or 5-pyrimidinyl, 2-pyrazinyl, and the like. The corresponding fully saturated and partially saturated radicals are also included, e.g. 2-piperazine. The heterocyclic radical is bonded through an available carbon atom in the heterocyclic ring. The radical may be optionally substituted with substituents at positions that do not significantly interfere with the preparation of compounds falling within the scope of this invention and that do not significantly reduce the efficacy of the compounds. The ring is optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, lower alkylcarbonylamino, or optionally-susbstituted phenyl or benzyl. Examples of 6-membered heterocycles include the following:

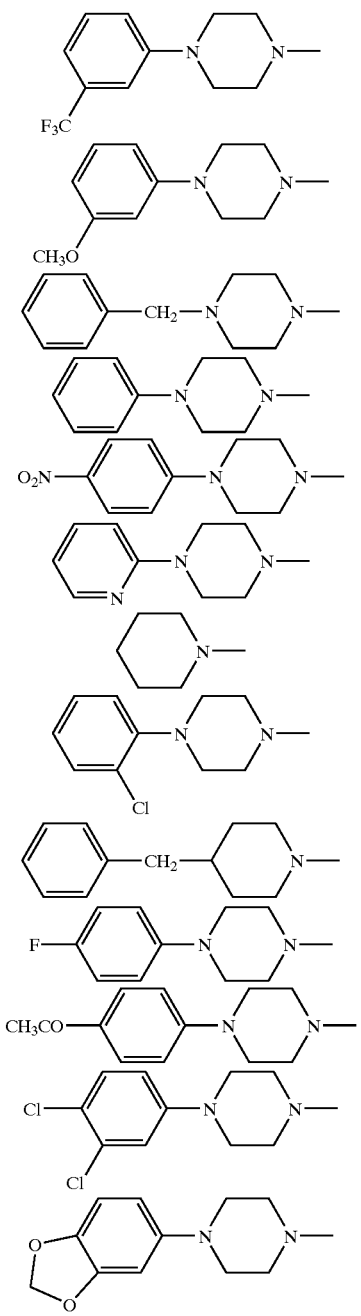

A fused heterocyclic system is a cyclic ring having a hetero atom such as nitrogen, oxygen, or sulfur, fused to another, heterocyclic or carbocyclic ring or rings. Representative examples the hetero ring include, e.g., 1-pyrrolidino, 1-piperidino, morpholino, piperazino, 3-benzopiperidino, and the like. These are fused to other rings and may be substituted or unsubstituted. If substituted, generally they will have no more than 2 substituents chosen from lower alkyl, lower cycloalkyl, alkoxy, hydroxy, halo, cyano, hydroxy lower alkyl, phenyl (substituted or unsubstituted), benzyl (substituted or unsubstituted), aminocarbonylmethyl, lower alkylaminocarbonylmethyl, amino, mono-or di-lower alkylamino, cyclic amino, or a 5- or 6-membered heterocyclic ring, and the like. An example is the following:

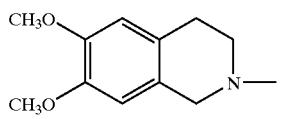

An "imide ring" is a cyclic imide wherein the nitrogen of the cyclic structure is bonded on each side to a carbonyl group, which in turn is bound to carbon atoms to form a ring. An imide ring would include, e.g. phthalimide (which may be substituted on the benzene ring) maleimide, 1,8- naphthalimide (which maybe substituted on the naphthyl ring—e.g 3-nitro-1,8-naphthalimide, 4-nitronaphalimide, 4-bromo-napthalimide, and the like). Others will be apparent to one of skill in the art. Examples of an imide ring include the following:

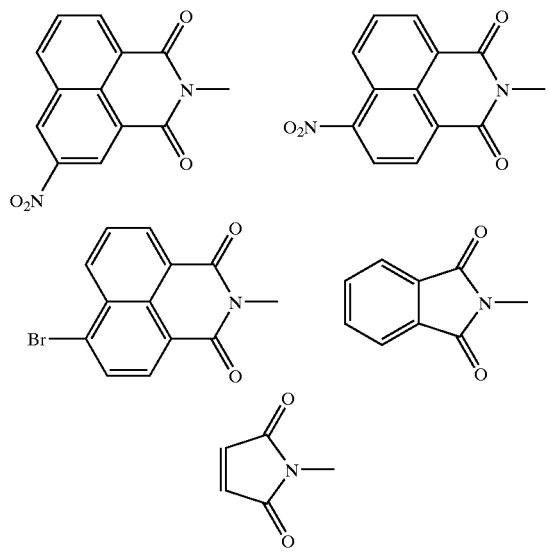

Other chemical terms are given their standard meaning as understood by one of skill in the art with guidance from standard texts and dictionaries.

The term "MTD" is the abbreviation for maximum tolerated does.

The term "nM" is the abbreviationfor nanomolar.

The term "ip" is the abbreviation for intraperitonial.

Compounds of the Invention

One aspect of this invention is a compound of the formula

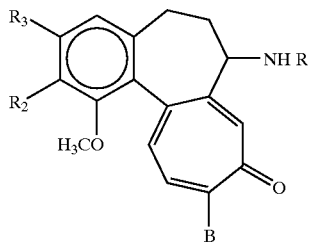

wherein

R is C(O)—(CHR$_4$)$_m$—A—R$_1$ where
m is 1–10,
A is S, O, N or a covalent bond,
R$_1$ is substituted phenyl or substituted benzoyl;
B is methoxy or methylthio;
R$_2$ is methoxy, hydroxy, or methylenedioxy when taken together with R$_3$;
R$_3$ is methoxy, hydroxy, a monosaccharide radical, or is methylenedioxy when taken together with R$_2$; and
R$_4$ is H or is H or methyl when m is 1.

Preferably the compound is represented by the above formula, wherein R$_2$ is methoxy, R$_3$ is a monsaccharide radical chosen from glucosyl and galactosidyl, and B is methythio. Alternatively B is methythio, R$_2$ is hydroxy or methoxy, and R$_3$ is hydroxy or methoxy, and preferably, R$_2$ and R$_3$ each is methoxy, particularly wherein m is 1 or 2 and A is S or O. For example, useful compounds include those wherein m is 1, A is O, and R$_1$ is 2,3,4,5,6-pentafluorophenyl or wherein m is 1 and R$_1$ is phenyl substituted with 1, 2, or 3 substituents chosen from, halo, methyl, methoxy, NO$_2$, trifluoromethyl, cyano, and an imide ring. Of the latter group, those of particular interest include compounds wherein R$_1$ is phenyl substituted with one or two halo substituents where A is O, or wherein R$_1$ is phenyl substituted with 1 or 2 methyl substituents or with 1 or 2 methoxy substituents. Another example is a compound wherein R$_1$ is benzoyl substituted with a halo, m is 1 or 2, B is methylthio, and A is a covalent bond.

Another aspect of this invention is a compound represented by the formula

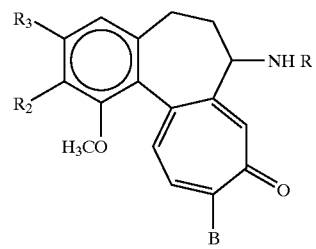

wherein

R is C(O)—(CHR$_4$)$_m$—A—R$_1$ where
m is 0–10,
A is oxygen, sulfur, nitrogen, or a covalent bond,
R$_1$ is phenyl substituted with one to five substituents (selected from halo, lower alkyl, cyano, nitro, amino, halogenated lower alkyl, carbonyl, hydroxycarbonyl, lower alkylcarbonyloxy, benzyloxy, optionally substituted 5 or 6 membered heterocyclic ring, an imide ring, lower alkoxycarbonyl, and lower alkylcarbonylamino), optionally substituted cycloalkyl of 3–7 carbons, optionally substituted naphtyl, an optionally substituted imide ring, an optionally substituted 5 or 6 member heterocycle with at least one N, S, or O in the ring, or an optionally substituted fused heterocyclic or fused carboxyclic ring system;
B is methoxy or methylthio;
R$_2$ is methoxy, hydroxy, or methylenedioxy when taken together with R$_3$;
R$_3$ is methoxy, hydroxy, a monosaccharide radical, or is methylenedioxy when taken together with R$_2$; and
R$_4$ is H or is H or methyl when m is 1.

Preferred is a compound wherein B is methylthio, R$_4$ is H, R$_2$ and R$_3$ each is methoxy; m is 0, 1 or 2; and A is oxygen, sulfur, or a covalent bond. Exemplary is a compound wherein R$_1$ is an optionally substituted 5-membered heterocycle with one, two, or three nitrogens in the ring, e.g. wherein R$_1$ is 1H-tetrazol-1-yl or 1-t-butoxycarbonylpyrrolidin-2-yl. Another exemplary compound is one wherein m is 0, A is a covalent bond, and $R_1$ is optionally substituted furan-2-yl, e.g. 5-nitrofuran-2-yl. Other preferred compounds are those wherein A is O or wherein m is 0, A is a covalent bond, and $R_1$ is phenyl substituted with an optionally substituted imide ring or alkyl-carbonylamino, e.g. $R_1$ is 4-phthalimidophenyl or 3-chloroacetylaminophenyl. Other compounds include those wherein $R_1$ is an optionally substituted 6-membered heterocycle with one or two nitrogens in the ring, particularly wherein A is a covalent bond and the 6-membered heterocycle is pyridine-3-yl, thymin-1-yl, or piperazin-1-yl, e.g. pyridin-3-yl, 4-(3-methoxyphenyl)piperazin-1-yl, or 4-(3-trifluoromethylphenyl)piperazin-1-yl. Other compounds include those wherein A is a covalent bond and $R_1$ is optionally substituted imide ring, e.g. phthalimido. Other compounds include those wherein $R_1$ is a fused heterocyclic ring system, for example wherein m is 0, A is a covalent bond, and $R_1$ is optionally substituted quinolin-4-yl, optionally substituted phenothiazin-10-yl, or optionally substituted naphthyrid-4-on-3-yl (e.g. $R_1$ is 2-phenylquinolin-4-yl, phenothiazin-10-yl, or 1,7-dimethyl-naphthyridin-4-on-3-yl) or the fused heterocyclic ring system is chromon-2-yl (particularly wherein m is 0 and A is a covalent bond). Other compounds are those wherein $R_1$ is a fused carbocyclic system, e.g. wherein m is 0, A is a covalent bond $R_1$ is anthraquinon-1-yl or wherein m is 1, A is oxygen and $R_1$ is 2,3,4,7-tetranitro-9-fluorenylideneamino. Still another example is a compound wherein m is 1, A is oxygen, an $R_1$ is quinolin-4-yl.

Another aspect of this invention is a compound represented by the formula

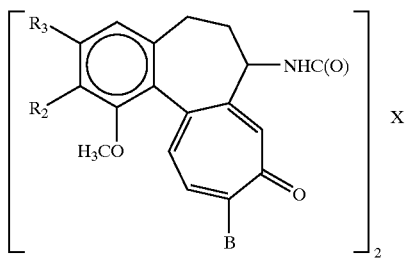

wherein

B is methoxy or methylthio;

$R_2$ is methoxy, hydroxy, or methylenedioxy when taken together with $R_3$;

$R_3$ is methoxy, hydroxy, a monosaccharide radical, or is methylenedioxy when taken together with $R_2$; and X is a linking group.

Preferred compounds are those wherein $R_2$ and $R_3$ each is methoxy and B is methylthio and X is 4-phenoxymethyl or X is 3,4-di(methoxyphenyl)-3,4-hexene.

Pharmaceutical Composition of the Invention

This aspect of the invention is a pharmaceutical composition useful for treating cancer in a warm-blooded animal, which composition comprises compound of the invention as defined herein in combination with a pharmaceutically acceptable excipient. The composition is prepared in accordance with known formulation techniques to provide a composition suitable for oral, topical, transdermal, rectal, by inhalation, parenteral (intravenous, intramuscular, or intraperitoneal) administration, and the like. Detailed guidance for preparing compositions of the invention are found by reference to the $18^{th}$ or $19^{th}$ Edition of Remington's Pharmaceutical. Sciences, Published by the Mack Publishing Co., Easton, Pa. 18040. The pertinent portions are incorporated herein by reference.

Unit doses or multiple dose forms are contemplated, each offering advantages in certain clinical settings. The unit dose would contain a predetermined quantity of active compound calculated to produce the desired effect(s) in the setting of treating cancer. The multiple dose form may be particularly useful when multiples of single doses, or fractional doses, are required to achieve the desired ends. Either of these dosing forms may have specifications that are dictated by or directly dependent upon the unique characteristic of the particular compound, the particular therapeutic effect to be achieved, and any limitations inherent in the art of preparing the particular compound for treatment of cancer.

A unit dose will contain a therapeutically effective amount sufficient to treat cancer in a subject and may contain from about 1.0 to 1000 mg of compound, for example about 50 to 500 mg.

The compound will preferably be administered orally in a suitable formulation as an ingestible tablet, a buccal tablet, capsule, caplet, elixir, suspension, syrup, trouche, wafer, lozenge, and the like. Generally, the most straightforward formulation is a tablet or capsule (individually or collectively designated as an "oral dosage unit"). Suitable formulations are prepared in accordance with a standard formulating techniques available that match the characteristics of the compound to the excipients available for formulating an appropriate composition. A tablet or capsule will preferably contain about 50 to about 500 mg of a compound of Formula (I).

The form may deliver a compound rapidly or may be a sustained-release preparation. The compound may be enclosed in a hard or soft capsule, may be compressed into tablets, or may be incorporated with beverages, food or otherwise into the diet. The percentage of the final composition and the preparations may, of course, be varied and may conveniently range between 1 and 90% of the weight of the final form, e.g., tablet. The amount in such therapeutically useful compositions is such that a suitable dosage will be obtained. Preferred compositions according to the current invention are prepared so that an oral dosage unit form contains between about 5.0 to about 50% by weight (% w) in dosage units weighing between 5 and 1000 mg.

The suitable formulation of an oral dosage unit may also contain: a binder, such as gum tragacanth, acacia, corn starch, gelatin; sweetening agents such as lactose or sucrose; disintegrating agents such as corn starch, alginic acid and the like; a lubricant such as magnesium stearate; or flavoring such a peppermint, oil of wintergreen or the like. Various other material may be present as coating or to otherwise modify the physical form of the oral dosage unit. The oral dosage unit may be coated with shellac, a sugar or both. Syrup or elixir may contain the compound, sucrose as a sweetening agent, methyl and propylparabens as a preservative, a dye and flavoring. Any material utilized should be pharmaceutically-acceptable and substantially non-toxic. Details of the types of excipients useful may be found in the nineteenth edition of "Remington: The Science and Practice of Pharmacy," Mack Printing Company, Easton, Pa. See particularly chapters 91–93 for a fuller discussion.

A compound may be administered parenterally, e.g., intravenously, intramuscularly, intravenously, subcutaneously, or interperitonically. The carrier or excipient or excipient mixture can be a solvent or a dispersive medium containing, for example, various polar or non-polar solvents, suitable mixtures thereof, or oils. As used herein "carrier" or "excipient" means a pharmaceutically acceptable carrier or excipient and includes any and all solvents, dispersive agents or media, coating(s), antimicrobial agents, iso/hypo/hypertonic agents, absorption-modifying agents, and the like. The use of such substances and the agents for pharmaceutically active substances is well known in the art. Except insofar as any conventional media or agent is incompatible with the active ingredient, use in therapeutic compositions is contemplated. Moreover, other or supplementary active ingredients can also be incorporated into the final composition.

Solutions of the compound may be prepared in suitable diluents such as water, ethanol, glycerol, liquid polyethylene glycol(s), various oils, and/or mixtures thereof, and others known to those skilled in the art.

The pharmaceutical forms suitable for injectable use include sterile solutions, dispersions, emulsions, and sterile powders. The final form must be stable under conditions of manufacture and storage. Furthermore, the final pharmaceutical form must be protected against contamination and must, therefore, be able to inhibit the growth of microorganisms such as bacteria or fungi. A single intravenous or intraperitoneal dose can be administered. Alternatively, a slow long term infusion or multiple short term daily infusions may be utilized, typically lasting from 1 to 8 days. Alternate day or dosing once every several days may also be utilized.

Sterile, injectable solutions are prepared by incorporating a compound in the required amount into one or more appropriate solvents to which other ingredients, listed above or known to those skilled in the art, may be added as required. Sterile injectable solutions are prepared by incorporating the compound in the required amount in the appropriate solvent with various other ingredients as required. Sterilizing procedures, such as filtration, then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

In all cases the final form, as noted, must be sterile and must also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

Prevention or inhibition of growth of microorganisms may be achieved through the addition of one or more antimicrobial agents such as chlorobutanol, ascorbic acid, parabens, thermerosal, or the like. It may also be preferable to include agents that alter the tonicity such as sugars or salts.

Although the compounds of this invention tend to be water soluble, in some cases, e.g., where a compound of the invention is less water soluble, it may be useful to provide liposomal delivery. The system restrains the compound of the invention by incorporating, encapsulating, surrounding, or entrapping the compound of the invention in, on, or by lipid vesicles or liposomes, or by micelles.

Liposomes have been used successfully to administer medications to cancer patients, and have been shown to be useful clinically in the delivery of anticancer drugs such as doxorubicin, daunorubicin, and cisplatinum complexes. Forssen, et al., *Cancer Res.* 1992, 52: 3255–3261; Perex-Soler, et al., *Cancer Res.* 1990, 50: 4260–4266; and, Khokhar, et al., *J. Med. Chem.* 1991, 34: 325–329, all of which are incorporated herein in their entireties by reference.

Similarly, micelles have also been used to deliver medications to patients, (Broden et al., *Acta Pharm Suec.* 19: 267–284 (1982)) and micelles have been used as drug carriers and for targeted drug delivery, (D. D. Lasic, *Nature* 335: 279–280 (1992); and, Supersaxo et al., *Pharm Res.* 8: 1280–1291 (1991)), including cancer medications, (Fung et al., *Biomater. Artif. Cells. Artif. Organs* 16: 439 et seq. (1988); and Yokoyama et al., *Cancer Res.* 51: 3229–3236 (1991)), al of which are incorporated herein in their entireties by reference.

The liposomes and/or micelles containing the compound of the invention can be administered to a cancer patient, typically intravenously. Further guidance for preparing liposomal compositions useful in this invention may be found in U.S. Pat. No. 6,096,336, which is incorporated herein by reference.

Method of Treatment of the Invention

Another aspect of this invention is a method for treating cancer in a warm-blooded animal, which method comprises administering a therapeutically effective amount of a compound of the invention as defined herein. A compound useful in this invention is administered to an appropriate subject in need of these compounds in a therapeutically effective dose by a medically acceptable route of administration such as orally, parentally (e.g., intramuscularly, intravenously, subcutaneously, intraperitoneally), transdermally, rectally, by inhalation and the like.

The term cancer is to be considered in the broadest general definition as a malignant neoplasm, an abnormal mass of tissue, the growth of which exceeds and is uncoordinated with that of normal tissues and persists in the same excessive manner after cessation of the stimuli that evoked the change. It might be added that the abnormal mass is purposeless, preys on the host, and is virtually autonomous. A cancer can also be considered as a malignant tumor. A further discussion of neoplasia is found at "Robbins Pathologic Basis of Disease," Sixth Edition, by R. S. Cotran, V. Kumar, and T. Collins, Chapter 8 (W.B. Saunders Company). This information from Chapter 8 is incorporated herein by reference. The following Table A provides examples of the types of cancers, i.e., malignant tumors or neoplasia that may be treated by administering a compound of this invention.

TABLE A

| Tissue of Origin | Malignant |
|---|---|
| Composed of One Parenchymal Cell Type | |
| Mesenchymal tumors | |
| Connective tissue and derivatives | Fibrosarcoma |
| | Liposarcoma |
| | Chondrosarcome |
| | Osteogenic sarcoma |
| Endothelial and related tissues | |
| Blood vessels | Angiosarcoma |
| Lymph vessels | Lymphangiosarcoma |
| Synovium | Synovial sarcoma |

TABLE A-continued

| Tissue of Origin | Malignant |
| --- | --- |
| Mesothelium | Mesothelioma |
| Brain coverings | Invasive meningioma |
| Blood cells and related cells | |
| Hematopoietic cells | Leukemias |
| Lymphoid tissue | Malignant lymphomas |
| Muscle | |
| Smooth | Leiomyosarcoma |
| Straited | Rhabdomyosarcoma |
| Epthelial tumors | |
| Stratified squamous | Squamous cell or epidermoid carcinoma |
| Basal cells of skin or adnexa | Basal cell carcinoma |
| Epithelial lining | |
| Glands or ducts | Adenocarcinoma |
| | Papillary carcinoma |
| | Cystadenocarcinoma |
| Respiratory passages | Bronchogenic carcinoma |
| | Bronchial adenoma (carcinoid) |
| Neuroectoderm | Malignant melanoma |
| Renal epithelium | Renal cell carcinoma |
| Liver cells | Hepatocellular carcinoma |
| Urinary tract epithelium (transitional) | Transitional cell carcinoma |
| Placental epithelium (trophoblast) | Choriocarcinoma |
| Testicular epithelium (germ cells) | Seminoma |
| | Embryonal carcinoma |
| More Than One Neoplastic Cell-Mixed Tumors, Usually Derived From One Germ Layer | |
| Salivary glands | Malignant mixed tumor of salivary gland origin |
| Breast | Malignant cystosarcoma phyllodes |
| Renal anlage | Wilms tumor |
| More Than One Neoplastic Cell Type Derived From More Than One Germ Layer-Teratogenous | |
| Totipotential cells in gonads or in embryonic rests | Immature teratoma, teratocarcinoma |

The compounds of the invention are thus useful in the treatment of leukemia and solid tumors, such as colon, colo-rectal, ovarian, mammary, prostate, lung, kidney and also melanoma tumors. The dosage range adopted will depend on the route of administration and on the age, weight and condition of the patient being treated. The compounds may be administered, for example, by the parenteral route, for example, intramuscularly, intravenously or by bolus infusion.

As used herein, a "therapeutically effective amount" of CPT derivatives of the present invention is intended to mean that amount of the compound which will inhibit the growth of, or retard cancer, or kill malignant cells, and cause the regression and palliation of malignant tumors, i.e., reduce the volume or size of such tumors or eliminate the tumor entirely.

With mammals, including humans, the effective amounts can be administered on the basis of body surface area. The interrelationship of dosages varies for animals of various sizes and species, and for humans (based on mg/m² of body surface) is described by E. J. Freireich et al., *Cancer Chemother. Rep.*, 50(4):219 (1966). Body surface area may be approximately determined from the height and weight of an individual (see, e.g., Scientific Tables, Geigy Pharmaceuticals, Ardsley, N.Y. pp. 537–538 (1970)). A suitable dose range is from 1 to 1000 mg of equivalent per m² body surface area of a compound of the invention, for instance from 50 to 500 mg/m².

For all of the administering routes, the exact timing of administration of the dosages can be varied to achieve optimal results. Generally, if using Intralipid 20 as the carrier for the derivative, the actual dosage of derivative reaching the patient will be less. This is due to some loss of the derivative on the walls of the syringes, needles and preparation vessels, which is prevalent with the Intralipid 20 suspension. When a carrier, such as cottonseed oil is used, this above described loss is not so prevalent because the derivative does not adhere as much to the surface of syringes, etc.

Another important feature of the method provided by the present invention relates to the relatively low apparent overall toxicity of the derivatives administered in accordance with the teachings herein. Overall toxicity can be judged using various criteria. For example, loss of body weight in a subject over 10% of the initially recorded body weight (i.e., before treatment) can be considered as one sign of toxicity. In addition, loss of overall mobility and activity and signs of diarrhea or cystitis in a subject can also be interpreted as evidence of toxicity.

Process of the Invention

Another aspect of this invention is process for preparing compounds of this invention by reacting an N-deacetylcolchicine or N-deacetylthiocolchicine with a compound of the formula $XC(O)(CHR_4)_mAR_1$, wherein m, A, $R_1$, and $R_4$, are as defined herein, and X is e.g. bromide, chloride, hydroxy, or alkoxy. Preferably X is OH. The compound shown as $XC(O)(CHR_4)_mAR_1$, can be referred to as a substituted alkanoic acid or substituted alkanoic acid derivative, e.g. where m is 1, it is substituted acetic acid or a derivative thereof, where m is 2, it is a substituted propionic acid or a derivative thereof, etc. One way that such an alkanoic acid is obtained is by reacting an appropriate $R_1AH$ compound with an omega-halosubstituted alkanoic acid ester (e.g. 3-halopropionic ester or 3-haloacetic ester), then hydrolyzing the ester to form the acid. Examples of preferred haloacetic acid or halopropionic acid esters include the ethyl ester of 2 or 3-bromo acid, 3-chloro acid, or 2 or 3-iodo acid. Other corresponding alkyl esters (e.g., methyl, propyl, and the like, are useful but ethyl is preferred). In some cases, it may be useful to prepare an acid halide from the corresponding alkanoic acid. The acid halides are obtained by reacting the corresponding acid with halogenated agents (such as $SOCl_2$, $PCl_3$, $POCl_3$, $PCl_5$, $PBr_3$, and so on). The acid chloride is preferred. Once the acid or its derivative is prepared, it is reacted with the appropriate N-deacetylcolchicine or N-deacetylthiocolchicine to form a compound of this invention. This reaction sequence can be generalized as follows:

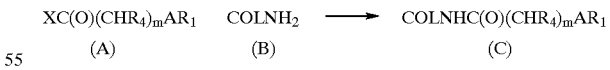

$$XC(O)(CHR_4)_mAR_1 \quad COLNH_2 \longrightarrow COLNHC(O)(CHR_4)_mAR_1$$
(A) (B) (C)

In the reaction sequence $COLNH_2$ represents N-deacetylcolchicine, N-deacetylthiocolchicine, or a modification thereof having the substituents at the 2- and 3-positions shown herein; X is hydroxy, halo, or alkoxy; m is an integer of 0–10; A is oxygen, sulfur, nitrogen, or a covalent bond; and $R_1$ and $R_4$ are as defined herein.

In the reaction sequence above, compound (A) will be used in molar excess of compound (B), e.g. a molar ratio of about 1.5:1 to about 4:1, preferably about 2:1 to 3:1. The reaction takes place in the presence of suitable coupling agent such as a carbodiimide compound, e.g.

disopropylcarbodiimide, but preferably 1-(3-dimethylaminopropyl)-3-ethyl carbodiimide hydrochloride (EDCI) and 4-(dimethylamino)pyridine (DMAP) in the presence of a suitable solvent, preferably a nonaqueous, nonpolar solvent. Examples of useful solvents in this step include halogenated alkane (e.g., dichoromethane or trichloromethane) and DMF. Dichloromethane is particularly useful. The reaction temperature will range from about 20° C. to about 40° C., preferably about 20° C. to about 25° C. The time needed for the reaction to be complete will generally be no more than about 20 hours, usually less than about 10 hours.

The N-deacetylcolchicine or N-diacetylthiocolchicine compounds may be substituted with substituents known in the art or that can be prepared by one of skill in the art given the disclosure herein. Representative articles that teach how to make such compounds or where such compounds may be procured are found in the following journals (which are incorporated herein by reference):

1. Dumont et al., *J. Med. Chem.* 1987, 30, 732–735.
2. Muzzaffar et al., *J. Med. Chem.* 1990, 33, 567–571.
3. Sun et al., *J. Med. Chem.* 1993, 36, 544–551.
4. Bombardelli, U.S. Pat. No. 5,777,136.
5. Bombardelli, U.S. Pat. No. 6,080,739
6. Shiau et al., *J. Pharm. Sci.* 1978, 67(3), 394–397.
7. Rösner et al., *J. Med. Chem.* 1981, 24, 257–261.
8. Gelmi et al., *J. Med. Chem.* 1999, 42, 5272–5276.

Suitable compounds include the following, where the number in parentheses following the name refers to journal article listed above:

N-deacetylcolchicine (8);
N-deacetylthiocolchicine (8);
N-deacetyl-2,3-methylenedioxycolchicine ($R_2$ and $R_3$ together are methylenedioxy, B is methoxy) (2);
N-deacetyl 2,3-methylenedioxythiocolchicine ($R_2$ and $R_3$ together are methylenedioxy, B is methythio) (2);
N-deacetyl-2,3-dihydroxycolchicine ($R_2=R_3=OH$, B is methoxy) (1);
N-deacetyl 2,3-dihydroxythiocolchicine ($R_2=R_3=OH$, B is methylthio) (1);
N-deacetyl-3-hydroxycolchicine ($R_2=B=$methoxy, $R_3$ is hydroxy) (2, 3, 4);
N-deacetyl-3-hydroxythiocolchicine ($R_2$ is methoxy, $R_3$ is hydroxy, B is methylthio) (2, 3, 4);
N-deacetyl-3-glucosylcolchicine ($R_2=B=$methoxy $R_3$ is glucosyl) (5, 6, 7);
N-deacetyl-3-glucosylthiocolchicine ($R_2$ is methoxy, $R_3$ is glucosyl, B is methylthio) (5, 6, 7);
N-deacetyl-3-galactosidylcolichicine ($R_2$ is methoxy, $R_3$ is galactosidyl, B is methoxy) (5, 6, 7);
N-deacetyl-3-galactosidylthiocolchicine ($R_2$ is methoxy, $R_3$ is galactosidyl, B is methylthio) (5, 6, 7);
and the like.

It will be recognized by one of skill in the art that other similar compounds may be prepared by following the teachings set forth in the above articles and modifying with appropriate art-recognized steps.

Suitable alkanoic acids of formula (A) are available commercially and include the following (see the catalog by the Sigma-Aldrich Corp., St. Louis, Mo. or www.sigmaaldrich.com):

4-fluorophenoxyacetic acid;
2,4-dimethylphenoxyacetic acid;
4-methoxyphenoxyacetic acid;
4-formylphenoxyacetic acid;
2-nitrophenoxyacetic acid;
5-nitro-2-furoic acid;
3-chloroacetaminobenzoic acid;
(4-pyridylthio)acetic acid;
chromone-2-carboxylic acid;
anthraquinone-2-carbonyl chloride;
1H-tetrazole-1-acetic acid;
(4-chlorophenylthio)acetic acid;
quinoline-4-oxyacetic acid;
4-nitrophenoxyacetic acid;
3,5-ditrifluoromethylphenoxyacetic acid;
4-trifluoromethoxyphenenoxyacetic acid;
4-bromophenoxyacetic acid;
4-iodophenoxyacetic acid;
phenoxyacetic acid;
2,4-dichloro-5-methylphenylthioacetic acid;
2,3,4,5,6-pentafluorophenoxyacetic acid;
3-fluoro-4-cyanophenoxyacetic acid;
3-trifluoromethyl-4-nitrophenoxyacetic acid;
4-phthalimidobenzoic acid;
3-chloro-4-bromophenoxy acetic acid;
2,6-diiodo-4-cyanophenoxyacetic acid;
4-(2-phenyl)quinolinecarboxylic acid;
phenothiazin-10-ylcarbonylchloride;
1,7-dimethyl-naphthyridin-4-one-3-carboxylic acid;
3-pyridinepropionic acid;
4-chlorophenoxyacetic acid;
3-methoxyphenoxyacetic acid;
thymine-1-acetic acid;
(+)-2-(2,4,5,7-tetranitro-9-fluorenylideneaminooxy) propionic acid;
3-phthalimidopropionic acid;
3-maleimidopropionic acid;
3-(3-nitro 1,8-naphthalimide)propionic acid;
3-(4-nito-1,8-naphthalimide)propionic acid;
3-(4-bromo-1,8-naphthalimido)propionic acid;
3-[4-(3-trifluoromethylphenyl)-1-piperazinyl]-propionic acid;
3-[(4-benzyl)-1-piperazinyl]propionic acid;
3-[4-(3-methoxyphenyl)-1-piperazinyl]propionic acid;
3-[4-(4-nitrophenyl)-1-piperazinyl]propionic acid;
3-(4-phenyl-1-piperazinyl)propionic acid;
3-[4-(2-chlorophenyl)-1-piperazinyl]propionic acid;
3-[4-(4-fluorophenyl)-1-piperazinyl]propionic acid;
3-(1-piperidino)propionic acid;
3-[1-(4-benzyl)piperidino]propionic acid;
3-[4-(4-acetylphenyl-1-piperazinyl]propionic acid;
3-[4-(3,4-dichlorophenyl)-1-piperazinyl]propionic acid;
3-[4-(3,4-methylenedioxyphenyl)-1-piperazinyl]propionic acid;
3-[4-(4-chlorophenyl)-1-piperidinyl]propionic acid;
3-(4-formyl-1-piperazinyl)propionic acid;
3-(4-ethyl-1-piperazinyl)propionic acid;
3-[4-(4-chlorophenyl)phenylmethyl-1-piperazinyl] propionic acid;
3-(4-cyano-4-phenyl-1-piperidinyl)propionic acid;
3-trans-4-cinnamyl-1-piperazinyl)propionic acid;
3-[4-(2-methylphenyl)-1-piperazinyl]propionic acid;
3-[4-(2,3-dimethylphenyl)-1-piperazinyl]propionic acid;
3-[4-(1-piperidino)-1-piperidino]propionic acid;
3-[4-(2-pyrimidinyl)-1-piperazinyl]propionic acid;
3-(4-cyclohexyl-1-piperazinyl)propionic acid;
3-[4-(α-(2-pyridyl)benzyl-1-piperazinyl]propionic acid;
3-(4-morpholino)propionic acid;
3-(1-pyrrolinyl)propionic acid;
4-[4-(3-trifluoromethylphenyl)-1-piperazinyl]butyric acid;

5-[4-(3-trifluoromethylphenyl)-1-piperazinly]valeric acid; and the like.

One of skill in the art will recognize that other similar 3-propionic acids and 2-acetic acids may be obtained from commercial sources or prepared by art-recognized procedures to be used in the process to prepare compounds of this invention. By reacting a compound shown in the list of N-deacetyl colchicine derivatives with a compound shown in the list of compounds of formula (A) in accordance with the guidelines for reaction condition, compounds of the invention will be obtained. These compounds will exhibit the desired characteristics to a greater or lesser extent. Guidance is provided herein as to the preferred subgroups of compounds within the family.

EXAMPLES AND PREPARATIONS

The following examples and preparations are given to provide methods for making representative compounds included as part of this invention. The examples also provide descriptions of in vitro and in vivo assays to aid in determining the utility of the compounds. Throughout the examples chemical formulas will be used to name compounds (e.g. $NaHCO_3$ is sodium bicarbonate) as appropriate. In naming the compounds, the compound is referred to as the N-substituted N-deacetyl thiocoichicine. The number given in parentheses after the name is a code number that corresponds to the test results shown in Example 40.

PREPARATIONS

Preparation 1
Synthesis of thiocolchicine

The mixture of colchicine (1.0 g, 2.5 mmol), $NaSCH_3$ (443 mg, 6.2 mmol) and water (50 ml) was stirred at room temperature for 72 h, then it was extracted with chloroform. Organic layer was washed with water and brine, dried over $MgSO_4$. after the removal of the solvent, the residue was separated by column chromatography (eluent: ethyl acetate and petroleum either) to afford 705 mg thiocolchicine, mp 180–182° C.

The chemical structure analysis was performed by $^1$HNMR ($CDCl_3$, 600 MHz): δ 7.95 (s, 1H, NH), 7.50 (d, 1H, H8), 7.35 (d, 1H, H12), 7.15 (d, 1H, H11), 6.60 (s, 1H, H4), 4.70 (m, 1H, H7), 3.91 (s, 6H, $OCH_3$), 3.66 (s, 3H, $OCH_3$), 2.44 (s, 3H, $SCH_3$), 3.00–2.20(m, 4H, H5, 6), 2.05 (s, 3H, $CH_3CO$).

Preparation 2
Synthesis of N-deacetylthiocolchicine

The reaction mixture of thiocolchicine (705 mg, 1.7 mmol), methanol (20 ml) and 2N hydrochloride (20 ml) was refluxed for 24 h. After cooling, the mixture was concentrated in vacuo. After water layer was acidified with sodium hydroxide solution to pH 10, it was extracted with chloroform. Organic layer was washed with water and brine, dried over MgSO4. After removal of the solvent, the residue was separated by column chromatography (eluent: ethyl acetate and ethanol) to give 320 mg N-deacetylthiocolchicine, mp 168–170° C.

The chemical structure analysis was performed by $^1$HNMR ($CDCl_3$, 600 MHz); δ 7.58 (s, 1H, H8), 7.19 (d, 1H, H12), 7.04 (d, 1H, H11), 6.55 (s, 1H, H4), 3.91 (s, 6H, $OCH_3$), 3.71 (t, 1H, H7), 3.66 (s, 3H, $OCH_3$), 2.44 (s, 3H, SCH3), 2.60–1.09(m, 6H, H5, 6 and $NH_2$).

Preparation 3
Synthesis of N-deacetylcolchicine

By sustituting colchicine for thiocolchine in Preparation 2, one obtains N-deacetylcolchicine

EXAMPLE 1
A. N-Deacetyl-N-(4-fluorophenoxyacetyl)thiocolchicine (000811)

The reaction mixture of N-deacetylthiocolchicine (24 mg, 0.053 mmol), 4-fluorophenoxyacetic acid (25.5 mg, 0.15 mmol), EDCI (25 mg, 0.13 mmol), DMAP (2 mg, 0.2 mmol) and dichloromethane (3 ml) was stirred at room temperature for 10 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 21 mg N-Deacetyl-N-(4-fluorophenoxyacetyl)thiocolchicine, mp 200–203°(dec.).

The chemical structure analysis was performed by $^1$HNMR ($CDCl_3$, 600 MHz); δ 7.28 (d, 1H, Ar—H), 7.19 (s, 1H, H7), 7.05 (m, 4H, NH, Ar—H and H11), 6.90 (d, 1H, Ar—H), 6.54 (s, 1II, H4), 4.70 (m, 1H, H7), 4.39 (q, 2H, $COCH_2O$, 3.95 (s, 3H, $OCH_3$), 3.91 (s, 3H, $OCH_3$), 3.68 (s, 3H, $OCH_3$), 2.44 (s, 3H, $SCH_3$), 2.60–1.80 (m, 4H, H5, 6).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;

N-deacetylthiocolchicine;

N-deacetyl-2,3-methylenedioxycolchicine ($R_2$ and $R_3$ together are methylenedioxy, B is methoxy);

N-deacetyl 2,3-methylenedioxythiocolchicine ($R_2$ and $R_3$ together are methylenedioxy, B-is methythio);

N-deacetyl-2,3-dihydroxycolchicine ($R_2=R_3=OH$, B is methoxy);

N-deacetyl 2,3-dihydroxycolchicine ($R_2=R_3=OH$, B is methylthio);

N-deacetyl-3-hydroxycolchicine ($R_2=R_3$=methoxy, $R_3$ is hydroxy);

N-deacetyl-3-hydroxythiocolchicine ($R_2$ is methoxy, $R_3$ is hydroxy, B is methylthio);

N-deacetyl-3-glucosylcolchicine ($R_2$=B=methoxy $R_3$ is glucosyl);

N-deacetyl-3-glucosylthiocolchicine ($R_2$ is methoxy, $R_3$ is glucosyl, B is methylthio);

N-deacetyl-3-galactosidylcolichicine ($R_2$ is methoxy, $R_3$ is galactosidyl, B is methoxy);

N-deacetyl-3-galactosidylthiocolchicine ($R_2$ is methoxy, $R_3$ is galactosidyl, B is methylthio); and the like.

EXAMPLE 2
A. N-Deacetyl-N-(2,5-dimethylphenoxyacetyl) thiocolchicine (000817)

The reaction mixture of N-deacetylthiocolchicine (22 mg, 0.06 mmol), 2,4-dimethlphenoxyacetic acid (25 mg, 0.13 mmol), DMAP (2 mg, 0.2 mmol) DMAP (2 mg, 0.2 mmol) and dichloromethane (3 ml) was stirred at room temperature for 10 h. Then dichloromethane (20 ml) was added. Organic layer was washed with $H_2O$, 5% $Na_2CO_3$ and brine, and then dried over $MgSO_4$. After the solvent was removed under vacuum, the residue was separated by column chromatography (eluent: ethyl acetate and petroleum ether) to afford 26.3 mg N-Deacetyl-N-(2,4-dimethylphenoxyacetyl) thiocolchicine, mp 85–87°(dec.).

The chemical structure analysis was performed by $^1$HNMR (CDCl$_3$, 600 MHz); δ 7.28 (d, 1H, H8), 7.18 (s, 1H, H12), 7.05–6.96 (m, 4H, NH, Ar-h and H11), 6.67 (d, 1H, Ar—H), 6.54 (s, 1H, H4), 4.70 (m, 1H, H7), 4.47, 4.38 (dd, 2H, COCH$_2$O), 3.95 (s, 3H, OCH$_3$), 3.91 (s, 3H, OCH$_3$), 3.68 (s, 3H, OCH$_3$), 2.44 (s, 3H, SCH$_3$), 2.30 (s, 3H, Ar—CH$_s$), 2.28 (s, 3H, Ar—CH$_3$), 2.60–1.09(m, 4H, H5, 6).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine (R$_2$ and R$_3$ together are methylenedioxy, B is methoxy);
N-deacetyl 2,3-methylenedioxythiocolchicine (R$_2$ and R$_3$ together are methylenedioxy, B-is methythio);
N-deacetyl-2,3-dihydroxycolchicine (R$_2$=R$_3$=OH, B is methoxy);
N-deacetyl 2,3-dihydroxycolchicine (R$_2$=R$_3$=OH, B is methylthio);
N-deacetyl-3-hydroxycolchicine (R$_2$=R$_3$=methoxy, R$_3$ is hydroxy);
N-deacetyl-3-hydroxythiocolchicine (R$_2$ is methoxy, R$_3$ is hydroxy, B is methylthio);
N-deacetyl-3-glucosylcolchicine (R$_2$=B=methoxy R$_3$ is glucosyl);
N-deacetyl-3-glucosylthiocolchicine (R$_2$ is methoxy, R$_3$ is glucosyl, B is methylthio);
N-deacetyl-3-galactosidylcolichicine (R$_2$ is methoxy, R$_3$ is galactosidyl, B is methoxy);
N-deacetyl-3-galactosidylthiocolchicine (R$_2$ is methoxy, R$_3$ is galactosidyl, B is methylthio); and the like.

EXAMPLE 3

A. N-Deacetyl-N-(4-methoxyphenoxyacetyl)thiocolchicine (000825)

The reaction mixture of N-deacetylthiocolchicine (15 mg, 0.04 mmol), 4-methoxyphenoxyacetic acid (14.5 mg, 0.08 mmol), EDCI (25 mg, 0.13 mmol), DMAP (2 mg, 0.2 mmol) and dichloromethane (3 ml) was stirred at room temperature for 20 h. Then dichloromethane (20 ml) was added. Organic layer was washed with H$_2$O, 5% Na$_2$CO$_3$ and brine, and then dried over MgSO$_4$. After the solvent was removed under vaccum, the residue was separated by column chromatography (eluent: ethyl acetate and petroleum ether) to afford 12 mg N-Deacetyl-N-(4-methoxyphenoxyacetyl) thiocolchicine, mp 110–112°(dec.).

The chemical structure analysis was performed by $^1$HNMR (CDCl$_3$, 600 MHz); δ 7.29 (d, 1H, H8), 7.17 (s, 1H, H12), 7.05 (m, 2H, NH and H11), 6.88 (s, 4H, Ar—H), 6.54 (s, 1H, H4), 4.70 (m, 1H, H7), 4.37 (q, 2H, COCH$_2$O), 3.95 (s, 3H, OCH$_3$), 3.91 (s, 3H, OCH$_3$), 3.79 (s, 3H, OCH$_3$), 3.68 (s, 3H, OCH$_3$), 2.46 (s, 3H, SCH$_3$), 2.60–1.26 (m, 4H, H5,6).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine (R$_2$ and R$_3$ together are methylenedioxy, B is methoxy);
N-deacetyl 2,3-methylenedioxythiocolchicine (R$_2$ and R$_3$ together are methylenedioxy, B-is methythio);
N-deacetyl-2,3-dihydroxycolchicine (R$_2$=R$_3$=OH, B is methoxy);
N-deacetyl 2,3-dihydroxycolchicine (R$_2$=R$_3$=OH, B is methylthio);
N-deacetyl-3-hydroxycolchicine (R$_2$R$_3$=methoxy, R$_3$ is hydroxy);
N-deacetyl-3-hydroxythiocolchicine (R$_2$ is methoxy, R$_3$ is hydroxy, B is methylthio);
N-deacetyl-3-glucosylcolchicine (R$_2$=B=methoxy R$_3$ is glucosyl);
N-deacetyl-3-glucosylthiocolchicine (R$_2$ is methoxy, R$_3$ is glucosyl, B is methylthio);
N-deacetyl-3-galactosidylcolichicine (R$_2$ is methoxy, R$_3$ is galactosidyl, B is methoxy);
N-deacetyl-3-galactosidylthiocolchicine (R$_2$ is methoxy, R$_3$ is galactosidyl, B is methylthio); and the like.

EXAMPLE 4

A. N-Deacetyl-N-(4-formylphenoxyacetyl)thiocolchicine (000829)

The reaction mixture of N-deacetylthiocolchicine (15 mg, 0.04 mmol), 4-formylphenoxyacetic acid (12 mg, 0.067 mmol), EDCI (25 mg, 0.13 mmol), DMAP (2 mg, 0.2 mmol) and dichloromethane(ml) was stirred at room temperature for 20 h. Then dichloromethane (20 ml) was added. Organic layer was washed with H$_2$O, 5% Na$_2$CO$_3$ and brine, and then dried over MgSO$_4$. After the solvent was removed under vaccum, the residue was separated by column chromatography (eluent: ethyl acetate and petroleum either) to afford 13.5 mg N-Deacetyl-N-(4-formylphenoxyacetyl) thiocolchicine, mp 78–80°(dec.).

The chemical structure analysis was performed by $^1$HNMR (CDCl$_3$, 600 MHz); δ 9.32 (s, 1H, CHO), 7.89 (d, 2H, Ar—H), 7.29 (d, 1H,H8), 7.20 (s, 2H, NH and H12), 7.05 (d, 3H, Ar—H and H11), 6.55 (s, 1H, H4), 4.70 (m, 1H, H7), 4.55 (q, 2H, COCH$_2$O), 3.95 (s, 3H, OCH$_3$), 3.91 (s, 3H, OCH$_3$), 3.68 (s, 3H, OCH$_3$), 2.44 (s, 3H, SCH$_3$), 2.60–1.26 (m, 4H, H5,6).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine (R$_2$ and R$_3$ together are methylenedioxy, B is methoxy);
N-deacetyl 2,3-methylenedioxythiocolchicine (R$_2$ and R$_3$ together are methylenedioxy, B-is methythio);
N-deacetyl-2,3-dihydroxycolchicine (R$_2$=R$_3$=OH, B is methoxy);
N-deacetyl 2,3-dihydroxycolchicine (R$_2$=R$_3$=OH, B is methylthio);
N-deacetyl-3-hydroxycolchicine (R$_2$=R$_3$=methoxy, R$_3$ is hydroxy);
N-deacetyl-3-hydroxythiocolchicine (R$_2$ is methoxy, R$_3$ is hydroxy, B is methylthio);
N-deacetyl-3-glucosylcolchicine (R$_2$=B=methoxy R$_3$ is glucosyl);
N-deacetyl-3-glucosylthiocolchicine (R$_2$ is methoxy, R$_3$ is glucosyl, B is methylthio);
N-deacetyl-3-galactosidylcolichicine (R$_2$ is methoxy, R$_3$ is galactosidyl, B is methoxy);
N-deacetyl-3-galactosidylthiocolchicine (R$_2$ is methoxy, R$_3$ is galactosidyl, B is methylthio); and the like.

EXAMPLE 5
A. N-Deacetyl-N-(2-nitrophenoxyacetyl)thiocolchicine (000830)

The reaction mixture of N-deacetylthiocolchicine (15 mg, 0.04 mmol), 2-nitrophenoxyacetic acid (15.8 mg, 0.08 mmol), EDCI (25 mg, 0.13 mmol), DMAP (2 mg, 0.2 mmol) and dichloromethane (3 ml) was stirred at room temperature for 20 h> Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 13 mg N-Deacetyl-N-(2-nitrophenoxyacetyl)thioclochicine, mp 242–244°(dec.).

The chemical structure analysis was performed by $^1$HNMR ($CDCl_3$, 600 MHz): δ 8.09 (d, 1H, Ar—H), 7.89 (d, 1H, Ar—H), 7.65 (t, 1H, Ar—H), 7.27 (d, 1H, H8), 7.18, 7.16 (m, 2H, NH and H12), 7.04 (t, 2H, H11 and Ar—H), 6.56 (s, 1H, H4), 4.64 (m, 1H, H7), 4.66, 4.54 (dd, 2H, $COCH_2O$). 3.95 (s, 3H, $OCH_3$), 3.91 (s, 3H, $OCH_3$), 3.67 (s, 3H, $OCH_3$), 2.42 (s, 3H, $SCH_3$), 2.60–1.26 (m, 4H, H5, 6).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine $R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2=R_3$=OH, B is methoxy);
N-deacetyl 2,3-dihydroxycolchicine ($R_2=R_3$=OH, B is methylthio);
N-deacetyl-3-hydroxycolchicine ($R_2=R_3$=methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2$=B=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 6
N-Deacetyl-N-(5-nitro-2-furnancarbonyl)thiocolchicine (000906)

The reaction mixture of N-deacetylthiocolchicine (15 mg, 0.04 mmol), 5-nitro-2-furoic acid (12.5 mg, 0.08 mmol), EDCI (25 mg, 0.13 mmol), DMAP (2 mg, 0.2 mmol) and dichloromethane (3 ml) was stirred at room temperature for 20 h. Then dichloromethane (20 ml) was added. Organic layer was washed with O, 5% $Na_2CO_3$ and brine, and then dried over $MgSO_4$. After the solvent was removed under vaccum, the residue was separated by column chromatography (eluent: ethyl acetate and petroleum ether) to afford 14 mg N-Deacetyl-N-(5-nitro-2-furancarbonyl)thioclochicine, mp 168–170° C.

The chemical structure analysis was performed by $^1$HNMR ($CDCl_3$, 600 MHZ: δ 9.32 (s, 1H, NH, 7.63 (s, 1H, Ar—H), 7.37 (t, 1H, H8), 7.18 (d, 1H,, H12), 7.14 (s, 2H, NH and H11), 6.85 (s, 1H, Ar—H), 6.57 (s, 1H, H4), 4.80 (m, 1H, H7), 3.96 (s, 3H, $OCH_3$), 3.92 (s, 3H, $OCH_3$), 3.67 (s, 3H, $OCH_3$), 2.42 (s, 3H, $SCH_3$), 2.60–1.26 (m, 4H, H5, 6).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2=R_3$=OH, B is methoxy);
N-deacetyl 2,3-dihydroxycolchicine ($R_2=R_3$=OH, B is methylthio);
N-deacetyl-3-hydroxycolchicine ($R_2=R_3$=methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2$=B=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 7
N-Deacetyl-N-(3-chloroacetaminobenzoyl)thiocolchicine (000911)

The reaction mixture of N-deactylthiocolchicine (15 mg, 0.04 mmol), 3-chloroacetaminobenzoic acid (17 mg, 0.08 mmol), EDCI (25 mg, 0.13 mmol), DMAP (2 mg, 0.2 mmol) and dichloromethane (3 ml) was stirred at room temperature for 20 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 14 mg N-Deacetyl-N-(3-chloroacetaminobenzoyl) thioclochicine, mp 138–140° C.

The chemical structure analysis was performed by $^1$HNMR (, 600 MHz); δ 8.38 (m, 2H, NH and Ar—H), 7.72 (d, 1H, Ar—H), 7.67 (s, 1H, Ar—H), 7.58 (s, 1H, Ar—H), 7.55 (d, 111, H8), 7.37 (d, 1H, H12), 7.15 (m, 2H, h11 and NH), 6.57 (s, 1H, H4), 4.85 (m, 1H, H7), 4.12 (q, 2H, $COCH_2cl$), 3.96 (s, 3H, $OCH_3$), 3.92 (s, 3H, $OCH_3$), 3.75 (s, 3H, $OCH_3$), 2.44 (s, 3H, $SCH_3$) 2.60–1.26 (m, 4H, H5,6).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);

N-deacetyl-2,3-dihydroxycolchicine ($R_2=R_3=OH$, B is methoxy);

N-deacetyl 2,3-dihydroxycolchicine ($R_2=R_3=OH$, B is methylthio);

N-deacetyl-3-hydroxycolchicine ($R_2=R_3=$methoxy, $R_3$ is hydroxy);

N-deacetyl-3-hydroxythiocolchicine ($R_2$ is methoxy, $R_3$ is hydroxy, B is methylthio);

N-deacetyl-3-glucosylcolchicine ($R_2=B=$methoxy $R_3$ is glucosyl);

N-deacetyl-3-glucosylthiocolchicine ($R_2$ is methoxy, $R_3$ is glucosyl, B is methylthio);

N-deacetyl-3-galactosidylcolichicine ($R_2$ is methoxy, $R_3$ is galactosidyl, B is methoxy);

N-deacetyl-3-galactosidylthiocolchicine ($R_2$ is methoxy, $R_3$ is galactosidyl, B is methylthio); and the like.

EXAMPLE 8

A. N-Deacetyl-N-(4-pyridylthioacetyl)thiocolchicine (000922)

The reaction mixture of N-deacetylthiocolchicine (15 mg, 0.04 mmol), (4-pyridylthio)acetic acid (13.5 mg, 0.08 mmol), EDCI (25 mg, 0.13 mmol), DMAP (2 mg, 0.2 mmol) and dichloromethane (3 ml) was stirred at room temperature for 20 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 14.5 mg N-Deacetyl-N-(4-pyridylthioacetyl)thiocolchicine, mp 185–190°(dec.)

The chemical structure analysis was performed by $^1$HNMR ($CDCl_3$, 600 MHz); δ 8.40 (s, 2H, Ar—H), 8.00 (bs, 1H, NH), 7.36 (b, 1H, Ar—H), 7.32 (d, 1H, Ar—H), 7.15 (d, 2H, Ar—H), 7.06 (d, 1H, H11), 6.52 (s, 1H, Ar—H), 4.70 (m, 1H, H7), 3.95 (s, 3H, $OCH_3$, 3.90 (s, 3H, $OCH_3$), 3.77 (q, 211, $SCH_2CO$), 3.67 (s, 3H, $OCH_3$), 2.43 (s, 3H, $SHC_3$), 2.60–1.26 (m. 4H, H5, 6).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2=R_3=OH$, B is methoxy);
N-deacetyl 2,3-dihydroxycolchicine ($R_2=R_3=OH$, B is methylthio);
N-deacetyl-3-hydroxycolchicine ($R_2=R_3=$methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2=B=$methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 9

A. N-Deacetyl-N-(chromone-2-carbonyl)thiocolchicine (000914)

The reaction mixture of N-deacetylthiocolchicine. (15 mg, 0.04 mmol), chromone-2-carboxylic acid (15 mg, 0.08 mmol), EDCI (25 mg, 0.13 mmol), DMAP (2 mg, 0.2 mmol) and dichloromethane (3 ml) was stirred at room temperature for 20 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 14.2 mg N-Deacetyl-N-(chromone-2-carbonyl) thiocolchicine, mp 200–202°(dec.).

The chemical structure analysis was performed by $^1$HNMR ($CDCl_3$, 600 MHz); δ 8.73 (d, 1H, Ar—H), 8.08 (dd, 1H, Ar—H), 7.61 (t, 1H, Ar—H), 7.55 (s, 1H, H8), 7.37 (m, 3H, H12, NH and Ar—H), 7.15 (d, 1H, H11), 6.82 (s, 1H, H4), 6.57 (s, 1H, Ar—H), 4.95 (m, 1H, H7), 3.97 (s, 311, $OCH_3$), 3.92 (s, 3H, $OCH_3$), 3.75 (s, 3H, $OCR_3$), 2.45 (s, 3H, $SCH_3$), 2.60–1.26 (m, 4H, H5,6).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2=R_3=OH$, B is methoxy);
N-deacetyl 2,3-dihydroxycolchicine ($R_2=R_3=OH$, B is methylthio);
N-deacetyl-3-hydroxycolchicine ($R_2=R_3=$methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2=B=$methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 10

A. N-Deacetyl-N-(anthraquinone-2-carbonyl)thiocolchicine (000908)

The reaction mixture of N-deacetylthiocolchicine (15 mg, 0.04 mmol), anthraquinone-2-carbonyl chloride (21.6 mg, 0.08 mmol), triethylamine (40 mg, 0.04 mmol) and dichloromethane (5 ml) was stirred at room temperature for 2 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 18 mg N-Deacetyl-N-(anthraquinone-2-carbonyl) thiocolchicine, mp 140–142°(dec.).

The chemical structure analysis was performed by $^1$HNMR ($CDCl_3$, 600 MHz): δ8.65 (s, 1H, Ar—H), 8.56 (b, 1H, NH), 8.40–8.00 (m, 4H, Ar—H), 7.75 (m, 2H, Ar—H), 7.62 (d, 1H, H8), 7.39 (D, 1H, H12), 7.15 (D, 1H, H11), 6.58 (S, 1H, H4), 4.95 (M, 1H, H7), 3.98 (S, 3H, $OCH_3$), 3.92 (S, 3H, $OCH_3$), 3.77 (S, 3H, $OCH_3$), 2.46 (2, 3H, $SCH_3$), 2.60–1.26 (M, 4H, H5, 6).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2=R_3=OH$, B is methoxy);
N-deacetyl 2,3-dihydroxycolchicine ($R_2=R_3=OH$, B is methylthio);
N-deacetyl-3-hydroxycolchicine ($R_2=R_3=$methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2=B=$methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 11

A. N-Deacetyl-N-(1H-tetrazole-1-acetyl)thiocolchicine (000918)

The reaction mixture of N-deacetylthiocolchicine (15 mg, 0.04 mmol), 1H-tetrazole-1-acetic acid (10 mg, 0.08 mmol), EDCI (25 mg, 0.13 mmol), DMAP (2 mg, 0.2 mmol) and dichloromethane (3 ml) was stirred at room temperature for 20 h. Then dichloromethane (20 ml) was added. Organic layer was washed with $H_2O$, 5% $Na_2CO_3$ and brine, and then drive over $MgSO_4$. After the solvent was removed under vaccum, the residue was separated by column chromatography (eluent: ethyl acetate and petroleum ether) to afford 12.1 mg N-Deacetyl-N-(1H-tetrazole-1-acetyl) thiocolchicine, mp 113–115°(dec.).

The chemical structure analysis was performed by $^1$HNMR ($CDCl_3$, 600 MHz), δ 9.26 (d, 1H, NH), 8.95 (s, 1H, tetra-H), 7.67 (s, 1H, H8, 7.40 (d, 1H, H12), 7.18 (d, 1H, H11), 6.55 (s, 1H, Hr), 4.79 (m, 1H, H7), 3.93 (s, 3H, $OCH_3$), 3.91 (s, 3H, $OCH_3$), 3.64 (s, 3H, $OCH_3$), 2.46 (s, 3H, $SCH_3$), 2.60–1.60 (m, 4H, H5,6).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2=R_3=OH$, B is methoxy);
N-deacetyl 2,3-dihydroxycolchicine ($R_2=R_3=OH$, B is methylthio);
N-deacetyl-3-hydroxycolchicine ($R_2=R_3=$methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2=B=$methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 12

A. N-Deacetyl-N-[(4-chlorophenylthio)acetyl] thiocoichicine (000921)

The reaction mixture of N-deacetylthiocolchicine (15 mg, 0.04 mmol), (4-chlorophenylthio)acetic acid (16 mg, 0.08 mmol), EDCI (25 mg, 0.13 mmol), DMAP (2 mg, 0.2 mmol) and dichloromethane (3 ml) was stirred at room temperature for 20 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 16.2 mg N-Deacetyl-N-[(4-chlorophenylthio)acetyl] thiocoichicine, mp 95–97° C.

The chemical structure analysis was performed by $^1$HNMR ($CDCl_3$, 600 MHz); δ 7.55 (bs, 1H, NH), 7.25 (m, 6H, Ar-h), 7.05 (d, 1H, H11), 6.52 (s, 1H, H4), 4.62 (m, 1H,H7), 3.94 (s, 3H, $OCH_3$), 3.90 (s, 3H, $OCH_3$), 3.66 (s, 3H, $OCH_3$), 3.61 (1, 2H, $SCH_2CO$), 2.43 (s, 3H, $SCH_3$), 2.60–1.60 (m, 4H, H5, 6).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2=R_3=OH$, B is methoxy);
N-deacetyl 2,3-dihydroxycolchicine ($R_2=R_3=OH$, B is methylthio);
N-deacetyl-3-hydroxycolchicine ($R_2=R_3=$methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2=B=$methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 13
A. N-Deacetyl-N-(quinoline-4-oxyacetyl)thiocolchicine (001201)

The reaction mixture of N-deacetylthiocolchicine (15 mg, 0.04 mmol), quinoline-4-oxyacetic acid (16 mg, 0.08 mmol), EDCI (25 mg, 0.13 mmol), DMAP (2 mg, 0.2 mmol) and dichloromethane (3 ml) was stirred at room temperature for 20 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 14.3 mg N-Deacetyl-N-(quinoline-4-oxyacetyl) thiocolchicine, mp 188–190°(dec.).

The chemical structure analysis was performed by $^1$HNMR (CDCl$_3$, 600 MHz); δ 8.95 (d, 1H, NH), 8.31 (d, 1H, Ar—H), 7.60 (m, 3H, Ar—H), 7.47 (d, 1H, Ar—H), 7.32 (m, 2H, Ar—H), 7.10 (d, 1H, H11), 6.52 (s, 1H, H4), 6.18 (d, 1H, Ar—H), 4.90 (q, 2H, 0OCH$_2$CO), 4.76 (m, 1H, H7), 3.91 (s, 3H, OCH$_3$), 3.89 (s, 3H, OCH$_3$), 3.63 (s, 3H, OCH$_3$), 2.44 (s, 3H, SCH$_3$), 2.60–1.80 (m, 4H, H5,6).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2=R_3=$OH, B is methoxy);
N-deacetyl 2,3-dihydroxycolchicine ($R_2=R_3=$OH, B is methylthio);
N-deacetyl-3-hydroxycolchicine ($R_2=R_3=$methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2=B=$methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 14
A. N-Deacetyl-N-(4-nitrophenoxyacetyl)thiocolchicine (001127)

The reaction mixture of N-deacetylthiocolchicine (15 mg, 0.04 mmol), 4-nitrophenoxyacetic acid (15 mg, 0.08 mmol), EDCI (25 mg, 0.13 mmol), DMAP (2 mg, 0.2 mmol) and dichloromethane (3 ml) was stirred at room temperature for 20 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 20.7 mg N-Deacetyl-N-(4-nitrophenoxyacetyl) thiocolchicine, mp 135–138° C.

The chemical structure analysis was performed by $^1$HNMR (CDCl$_3$, 600 MHz): δ 8.23 (d, 2H, Ar—H), 7.45 (bs, 1H, NH), 7.30 (d, 1H, Ar—H), 7.27 (s, 1H, Ar—H), 7.08 (d, 1H, Ar—H), 7.034 (d, 2H, H11 and Ar—H), 6.55 (s, 1H, H4), 4.75 (m, 1H, H7), 4.54 (1, 2H, COCH$_2$O), 3.95 (s, 3H, OCH$_3$), 3.91 (s, OCH$_3$), 3.68 (s, 3H, OCH$_3$), 2.44 (s, 3H, SCH$_3$), 2.60–180 (m, 4H, H5,6).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocoichicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2=R_3=$OH, B is methoxy);
N-deacetyl 2,3-dihydroxycolchicine ($R_2=R_3=$OH, B is methylthio);
N-deacetyl-3-hydroxycolchicine ($R_2=R_3=$methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2=B=$methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 15
A. N-Deacetyl-N-(3,5-di-trifluoromethylphenoxyacetyl) thiocolchicine (001207)

The reaction mixture of N-deacetylthiocolchicine (15 mg. 0.04 mmol), 3,5-ditrifluoromethylphenoxyacetic acid (17 mg, 0.06 mmol), EDCI (25 mg, 0.13 mmol), DMAP (2 mg, 0.2 mmol) and dichloromethane (3 ml) was stirred at room temperature for 20 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 12.5 mg N-Deacetyl-N-(3,5-ditrifluoromethylphenoxyacetyl)thiocolchicine, mp 108–110° C.

The chemical structure analysis was performed by $^1$HNMR (CDCl$_3$, 600 MHz): δ 7.71 (d, 1H, Ar—H), 7.54 (s, 1H, Ar—H), 7.35 (m, 4H, Ar—H and NH), 7.08 (d, 1H, H11), 6.56 (s, 1H, 114), 4.80 (m, 1H, H7), 4.51 (q, 2H, COCJ$_2$O), 3.95 (s, 3H, OCH$_3$), 3.91 (s, 3H, OCH$_3$), 3.67 (s, 3H, OCH$_3$), 2.44 (s, 3H, SCH$_3$), 2.60–2.00 (m, 4H, H5,6).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);

N-deacetyl-2,3-dihydroxycolchicine ($R_2=R_3=OH$, B is methoxy);

N-deacetyl 2,3-dihydroxycolchicine ($R_2=R_3=OH$, B is methylthio);

N-deacetyl-3-hydroxycolchicine ($R_2=R_3$=methoxy, $R_3$ is hydroxy);

N-deacetyl-3-hydroxythiocolchicine ($R_2$ is methoxy, $R_3$ is hydroxy, B is methylthio);

N-deacetyl-3-glucosylcolchicine ($R_2$=B=methoxy $R_3$ is glucosyl);

N-deacetyl-3-glucosylthiocolchicine ($R_2$ is methoxy, $R_3$ is glucosyl, B is methylthio);

N-deacetyl-3-galactosidylcolichicine ($R_2$ is methoxy, $R_3$ is galactosidyl, B is methoxy);

N-deacetyl-3-galactosidylthiocolchicine ($R_2$ is methoxy, $R_3$ is galactosidyl, B is methylthio); and the like.

EXAMPLE 16

A. N-Deacetyl-N-(4-trifluoromethoxyphenoxyacetyl) thiocolchicine (001213).

The reaction mixture of N-deacetylthiocolchicine (15 mg., 0.04 mmol), 4-trifluoromethoxyphenoxyacetic acid (18 mg., 0.08 mmol), EDCI (25 mg, 0.13 mmol), DMAP (2 mg, 0.02 mmol) and dichloromethane (3 ml) was stirred at room temperature for 20 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 17.9 mg N-Deacetyl-N-(4-trifluoromethosyphenoxyacetyl)thiocolchicine, mp 90–92° C.

The chemical structure analysis was performed by $^1$HNMR (CDCl$_3$, 600 MHz): δ 7.29 (d, 1H, Ar—H), 7.22 (s, 1H, Ar—H), 7.18 (m, 3H, Ar—H and NH), 7.06 (d, 1H, H12), 6.94 (d, 1H, H11), 6.55 (s, 1H, H4), 4.73 (m, 1H, H7), 4.42 (q, 2H, COCH$_2$O), 3.95 (s, 3H, OCH$_3$), 3.91 (s, 311, OCH$_3)$, 3.68 (s, 3H, OCH$_3$), 2.43 (s, 3H, SCH$_3$), 2.60–1.80 (m, 4H, H5, 6).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;

N-deacetylthiocolchicine;

N-deacetyl-2,3-methylenedioxycolchicine ($R_2$ and $R_3$ together are methylenedioxy, B is methoxy);

N-deacetyl 2,3-methylenedioxythiocolchicine ($R_2$ and $R_3$ together are methylenedioxy, B-is methythio);

N-deacetyl-2,3-dihydroxycolchicine ($R_2=R_3=OH$, B is methoxy);

N-deacetyl 2,3-dihydroxycolchicine ($R_2=R_3=OH$, B is methylthio);

N-deacetyl-3-hydroxycolchicine ($R_2=R_3$=methoxy, $R_3$ is hydroxy);

N-deacetyl-3-hydroxythiocolchicine ($R_2$ is methoxy, $R_3$ is hydroxy, B is methylthio);

N-deacetyl-3-glucosylcolchicine ($R_2$=B=methoxy $R_3$ is glucosyl);

N-deacetyl-3-glucosylthiocolchicine ($R_2$ is methoxy, $R_3$ is glucosyl, B is methylthio);

N-deacetyl-3-galactosidylcolichicine ($R_2$ is methoxy, $R_3$ is galactosidyl, B is methoxy);

N-deacetyl-3-galactosidylthiocolchicine ($R_2$ is methoxy, $R_3$ is galactosidyl, B is methylthio); and the like.

EXAMPLE 17

A. N-Deacetyl-N-(3-pyridinepropionyl)thiocolchicine (000901).

The reaction mixture of N-deacetylthiocolchicine (15 mg, 0.04 mmol), 3-pyridinepropionic acid (12 mg, 0.08 mmol), EDCI (25 mg, 0.13 mmol), DMAP (2 mg, 0.02 mmol) and dichloromethane (3 ml) was stirred at room temperature for 20 h. Then dichloromethane (20 ml) was added. Organic layer was washed with $H_2O$, 5% $Na_2CO_3$ and bring, and then dried over $MgSO_4$. After the solvent was removed under vaccum, the residue was separated by column chromatography (eluent: ethyl acetate and petroleum ether) to afford 15.0 mg N-Deacetyl-N-(3-pyridinepropionyl) thiocolchicine, mp 88–90°(dec.)

The chemical structure analysis was performed by $^1$HNMR (CDCl$_3$, 600 MHz): δ 9.25 (d, 1H, Ar—H), 7.62 (s, 1H, Ar—H), 7.37 (d, 1H, Ar—H), 7.20 (t, 1H, Ar—H), 7.14 (s, 1H, Ar—H), 7.03 (d, 1H, H11), 6.58 (d, 1H, Ar—H), 6.51 (d, 2H, Ar—H), 6.44 (d, 1H, Ar—H), 4.62 (m, 1H, H7), 4.51 (q, 2H, COCH$_2$O), 3.94 (s, 3H, OCH$_3$), 3.91 (s, 3H, OCH$_3$), 3.80 (s, 3H, Ar—OCH$_3$), 3.65 (s, 3H, OCH$_3$), 3.29 (bs, 4H, NCH$_2$), 2.43 (m, 2H, CH$_2$CO), 2.41 (s, 3H SCH$_3$) 2.60–1.70 (m, 8H, H5,6 and COCH$_2$CH$_2$Ar).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;

N-deacetylthiocolchicine;

N-deacetyl-2,3-methylenedioxycolchicine ($R_2$ and $R_3$ together are methylenedioxy, B is methoxy);

N-deacetyl 2,3-methylenedioxythiocolchicine ($R_2$ and $R_3$ together are methylenedioxy, B-is methythio);

N-deacetyl-2,3-dihydroxycolchicine ($R_2=R_3=OH$, B is methoxy);

N-deacetyl 2,3-dihydroxycolchicine ($R_2=R_3=OH$, B is methylthio);

N-deacetyl-3-hydroxycolchicine ($R_2=R_3$=methoxy, $R_3$ is hydroxy);

N-deacetyl-3-hydroxythiocolchicine ($R_2$ is methoxy, $R_3$ is hydroxy, B is methylthio);

N-deacetyl-3-glucosylcolchicine ($R_2$=B=methoxy $R_3$ is glucosyl);

N-deacetyl-3-glucosylthiocolchicine ($R_2$ is methoxy, $R_3$ is glucosyl, B is methylthio);

N-deacetyl-3-galactosidylcolichicine ($R_2$ is methoxy, $R_3$ is galactosidyl, B is methoxy);

N-deacetyl-3-galactosidylthiocolchicine ($R_2$ is methoxy, $R_3$ is galactosidyl, B is methylthio); and the like.

EXAMPLE 18

A. N-Deacetyl-N-(4-chlorophenoxyacetyl)thiocolchicine (000814).

The reaction mixture of N-deacetylthiocolchicine (24 mg, 0.06 mmol), 4-chlorophenoxyacetic acid (25 mg. 0.13 mmol), EDCI (29 mg. 0.13 mmol), DMAP (2 mg, 0.02 mmol) and dichloromethane (3 ml) was stirred at room temperature for 20 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 24.3 mg N-Deacetyl-N-(4-chlorophenoxyacetyl)thiocolchicine, mp 88–90°(dec).

The chemical structure analysis was performed by $^1$HNMR (CDCl$_3$, 600 MHz): δ 7.28 (m, 3H, Ar—H), 7.20 (s, 1H, Ar—H), 7.13 (d, 1H, Ar—H), 7.05 (d, 1H, Ar—H) 6.55 (s, 1H, H4), 4.72 (m, 1H, H7), 4.45 (q, 2H, COCH$_2$O), 3.95 (s, 3H, OCH$_3$), 3.91 (s, 3H, OCH$_3$), 3.67 (s, 3H, OCH$_3$), 2.43 (s, 3H, SCH$_3$), 2.60–1.70 (m, 4H, H5,6).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;

N-deacetylthiocolchicine;

N-deacetyl-2,3-methylenedioxycolchicine (R$_2$ and R$_3$ together are methylenedioxy, B is methoxy);

N-deacetyl 2,3-methylenedioxythiocolchicine (R$_2$ and R$_3$ together are methylenedioxy, B-is methythio);

N-deacetyl-2,3dihydroxycolchicine (R$_2$=R$_3$=OH, B is methoxy);

N-deacetyl 2,3-dihydroxycolchicine (R$_2$=R$_3$=OH, B is methylthio);

N-deacetyl-3-hydroxycolchicine (R$_2$=R$_3$methoxy, R$_3$ is hydroxy);

N-deacetyl-3-hydroxythiocolchicine (R$_2$ is methoxy, R$_3$ is hydroxy, B is methylthio);

N-deacetyl-3-glucosylcolchicine (R$_2$=B=methoxy R$_3$ is glucosyl);

N-deacetyl-3-glucosylthiocolchicine (R$_2$ is methoxy, R$_3$ is glucosyl, B is methylthio);

N-deacetyl-3-galactosidylcolichicine (R$_2$ is methoxy, R$_3$ is galactosidyl, B is methoxy);

N-deacetyl-3-galactosidylthiocolchicine (R$_2$ is methoxy, R$_3$ is galactosidyl, B is methylthio); and the like.

EXAMPLE 19

A. N-Deacetyl-N-(3-methoxyphenoxyacetyl)thiocolchicine (001024).

The reaction mixture of N-deacetylthiocolchicine (15 mg, 0.05 mmol), 3-methoxyphenoxyacetic acid (14 mg, 0.08 mmol), EDCI (25 mg, 0.13 mmol), DMAP (2 mg, 0.02 mmol) and dichloromethane (3 ml) was stirred at room temperature for 20 h. Then dichloromethane (20 ml) was added. Organic layer was washed with H$_2$O, 5% Na$_2$CO$_3$ and brine, and then dried over MgSO$_4$. After the solvent was removed under vaccum, the residue was separated by column chromatography (eluent: ethyl acetate and petroleum ether) to afford 16.0 mg N-Diacetyl-N-(3-methoxyphenoxyacetyl)thiocolchicine, mp 182–18) to afford 16.0 mg N-Deacetyl-N-(3-methoxyphenoxyacetyl)thiocolchicine, mp 182–184° C.

The chemical structure analysis was performed by $^1$HNMR (CDCl$_3$, 600 MHz): δ 7.29 (d, 1H, Ar—H), 7.24 (t, 1H, Ar—H), 7.18 (s, 1H, Ar—H), 7.08 (d, 1H, Ar—H), 7.05 (d, 1H, Ar—H), 6.65 (d, 1H, Ar—H), 6.54 (s, 1H, H4), 6.51 (d, 2H, NH and Ar—H), 4.75 (m, 1H, H7), 4.43 (q, 2H, COCH$_2$O), 3.95 (s, 3H, OCH$_3$) 3.91 (s, 3H, OCH$_3$), 3.81 (s, 3H, OCH$_3$), 3.68 (s, 3H, OCH$_3$), 2.43 (s, 3H, SCH$_3$), 2.60–1.80 (m, 4H, H5,6).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;

N-deacetylthiocolchicine;

N-deacetyl-2,3-methylenedioxycolchicine (R$_2$ and R$_3$ together are methylenedioxy, B is methoxy);

N-deacetyl 2,3-methylenedioxythiocolchicine (R$_2$ and R$_3$ together are methylenedioxy, B-is methythio);

N-deacetyl-2,3-dihydroxycolchicine (R$_2$=R$_3$=OH, B is methoxy);

N-deacetyl 2,3-dihydroxycolchicine (R$_2$=R$_3$=OH, B is methylthio);

N-deacetyl-3-hydroxycolchicine (R$_2$=R$_3$=methoxy, R$_3$ is hydroxy);

N-deacetyl-3-hydroxythiocolchicine (R$_2$ is methoxy, R$_3$ is hydroxy, B is methylthio);

N-deacetyl-3-glucosylcolchicine (R$_2$=B=methoxy R$_3$ is glucosyl);

N-deacetyl-3-glucosylthiocolchicine (R$_2$ is methoxy, R$_3$ is glucosyl, B is methylthio);

N-deacetyl-3-galactosidylcolichicine (R$_2$ is methoxy, R$_3$ is galactosidyl, B is methoxy);

N-deacetyl-3-galactosidylthiocolchicine (R$_2$ is methoxy, R$_3$ is galactosidyl, B is methylthio); and the like.

EXAMPLE 20

A. N-Deacetyl-N-(thymine-1-acetyl)thiocolchicine (000905).

The reaction mixture of N-deacetylthiocolchicine (15 mg, 0.05 mmol), thymine-1-acetic acid (15 mg, 0.08 mmol), EDCI (25 mg, 0.13 mmol), DMAP (2 mg, 0.02 mmol) and dichloromethane (3 ml) was stirred at room temperature for 20 h. Then dichloromethane (20 ml) was added. Organic layer was washed with H$_2$O, 5% Na$_2$CO$_3$ and brine, and then dried over MgSO$_4$. After the solvent was removed under vaccum, the residue was separated by column chromatography (eluent: ethyl acetate and petroleum ether) to afford 24 mg N-Deacetyl-N-(thymine-1-acetyl)thiocolchicine, mp 195–197° C.

The chemical structure analysis was performed by $^1$HNMR (CDCl$_3$, 600 MHz): δ 8.96 (s. 111, NH), 8.84 (d, 1H, NH), 7.56 (s, 1H, H8), 7.33 (d, 1H, H11), 7.13 (d, 1H, Ar-11), ;7.10 (m, 211, Ar—H), 6.53 (s, 1H, H4), 4.75 (m, 1H, H7), 4.53 (q, 2H, COCH$_2$O), 3.94 (s, 3H, OCH$_3$), 2.60–1.70 (m, 4H, H5, 6).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;

N-deacetylthiocolchicine;

N-deacetyl-2,3-methylenedioxycolchicine (R$_2$ and R$_3$ together are methylenedioxy, B is methoxy);

N-deacetyl 2,3-methylenedioxythiocolchicine (R$_2$ and R$_3$ together are methylenedioxy, B-is methythio);

N-deacetyl-2,3-dihydroxycolchicine (R$_2$=R$_3$=OH, B is methoxy);

N-deacetyl 2,3-dihydroxycolchicine (R$_2$=R$_3$=OH, B is methylthio);

N-deacetyl-3-hydroxycolchicine (R$_2$=R$_3$=methoxy, R$_3$ is hydroxy);

N-deacetyl-3-hydroxythiocolchicine (R$_2$ is methoxy, R$_3$ is hydroxy, B is methylthio);

N-deacetyl-3-glucosylcolchicine (R$_2$=B=methoxy R$_3$ is glucosyl);

N-deacetyl-3-glucosylthiocolchicine (R$_2$ is methoxy, R$_3$ is glucosyl, B is methylthio);

N-deacetyl-3-galactosidylcolichicine (R$_2$ is methoxy, R$_3$ is galactosidyl, B is methoxy);

N-deacetyl-3-galactosidylthiocolchicine (R$_2$ is methoxy, R$_3$ is galactosidyl, B is methylthio); and the like.

EXAMPLE 21

A. N-Deacetyl-N-[(+)-2-(2,4,5,7-tetranitro-9-fluorenylideneaminooxy)propionyl]thiocolchicine (000913)

The reaction mixture of N-deacetylthiocolchicine (15 mg, 0.04 mmol), (+)-2-(2,4,5,7-tetranitro-9-fluorenylideneaminooxy)propionic acid (26 mg, 0.06 mmol), EDCI (25 mg, 0.13 mmol), DMAP (2 mg, 0.2 mmol) and dichloromethane (3 ml) was stirred at room temperature for 20 h. Then dichloromethane (20 ml) was added. Organic layer was washed with $H_2O$, 5% $Na_2CO$, and brine, and then dried over $MgSO_4$. After the solvent was removed under vaccum, the residue was separated by column chromatography (eluent; ethyl acetate and petroleum ether) to afford 18.4 mg N-Deacetyl-N-[(+)-2-(2,4,5,7-tetranitro-9-fluorenylideneaminooxy)propionyl]thiocolchicine, mp 205–208°(dec.).

The chemical structure analysis was performed by $^1$HNMR ($CDCl_3$, 600 MHz): δ 9.54 (s, 1H, Ar—H), 8.97 (s, 1H, Ar—H), 8.94 (s, 1H, Ar—H) 8.85 (s, 1H, Ar—H), 8.22 (s, 1H, NH), 7.18 (s, 1H, Ar—H), 7.11 (d, 1H, H11), 6.89 (d, 1H, Ar—H), 6.53 (s, 1H, H4), 5.36 (m, 1H, OCH), 4.75 (m, 1H, H7), 4.53 (q, 2H, $COCH_2O$), 3.94 (s, 3H, $OCH_3$), 3.91 (s, 3H, $OCH_3$), 3.71 (s, 3H, $OCH_3$), 2.23 (s, 3H, $SCH_3$), 1.88 (d, 3H, $CH_3$), 2.60–1.70 (m, 4H, H5,6).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2=R_3=OH$, B is methoxy);
N-deacetyl 2,3-dihydroxycolchicine ($R_2=R_3=OH$, B is methylthio);
N-deacetyl-3-hydroxycolchicine ($R_2=R_3$=methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2=B$=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 22

A. N-Deacetyl-N-(4-bromophenoxyacetyl)thiocoichicine (000815)

The reaction mixture of N-deacetylthiocolchicine (24 mg, 0.053 mmol), 4-bromophenoxyacetic acid (34.6 mg, 0.15 mmol), EDCI (29 mg), DMAP (3 mg) and dichloromethane (3 ml) was stirred at room temperature for 23 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 30 mg N-Deacetyl-N-(4-bromophenoxyacetyl)thiocolchicine, mp 108–110° C.

The chemical structure analysis was performed by $^1$HNMR ($CDCl_3$, 600 MHz).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2=R_3=OH$, B is methoxy);
N-deacetyl 2,3dihydroxycolchicine ($R_2=R_3=OH$, B is methylthio);
N-deacetyl-3-hydroxycolchicine ($R_2=R_3$=methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2=B$=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 23

A. N-Deacetyl-N-(4-iodophenoxyacetyl)thiocolchicine (000816)

The reaction mixture of N-deacetylthiocolchicine (24 mg, 0.064 mmol), 4-iodophenoxyacetic acid (41 mg, 0.15 mmol), EDCI (29 mg), DMAP (2 mg, 0.2 mmol) and dichloromethane (3 ml) was stirred at room temperature for 20 h. Then dichloromethane (20 ml) was added. Organic layer was washed with $H_2O$, 5% $Na_2CO_3$ and brine, and then dried over $MgSO_4$. After the solvent was removed under vacuum, the residue was separated by column chromatography (eluent: ethyl acetate and petroleum ether) to afford 35 mg N-Deacetyl-N-(4-iodophenoxyacetyl)thiocolchicine.

The chemical structure analysis was performed by $^1$HNMR ($CDCl_3$, 600 MHz).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2=R_3=OH$, B is methoxy);
N-deacetyl 2,3-dihydroxycolchicine ($R_2=R_3=OH$, B is methylthio);
N-deacetyl-3-hydroxycolchicine ($R_2=R_3$=methoxy, $R_3$ is hydroxy);
N-deacetyl-3-hydroxythiocolchicine ($R_2$ is methoxy, $R_3$ is hydroxy, B is methylthio);

N-deacetyl-3-glucosylcolchicine ($R_2$=B=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 24

A. N-Deacetyl-N-(4-methoxyphenoxyacetyl)thiocolchicine (000818)

The reaction mixture of N-deacetylthiocolchicine (17 mg, 0.045 mmol), phenoxyacetic acid (10.6 mg, 0.022 mmol), EDCI (16 mg, 0.084 mmol), DMAP (2 mg, 0.2 mmol) and dichloromethane (3 ml) was stirred at room temperature for 20 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 12 mg N-Deacetyl-N-(4-methoxyphenoxyacetyl) thiocolchicine.

The chemical structure analysis was performed by $^1$HNMR.

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2$=$R_3$=OH, B is methoxy);
N-deacetyl 2,3-dihydroxycolchicine ($R_2$=$R_3$=OH, B is methylthio);
N-deacetyl-3-hydroxycolchicine ($R_2$=$R_3$=methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2$=B=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 25

A. N-Deacetyl-N-(2,4-dichloro-5-methylphenylthioacetyl thiocolchicine (000831)

The reaction mixture of N-deacetylthiocolchicine (15 mg, 0.04 mmol), 2,4-dichloro-5-methylphenylthioacetic acid (20 mg, 0.08 mmol), EDCI (25 mg, 0.13 mmol), DMAP (2 mg, 0.2 mmol) and dichloromethane(ml) was stirred at room temperature for 20 h. Then dichloromethane (20 ml) was added. Organic layer was washed with $H_2O$, 5% $Na_2CO_3$ and brine, and then dried over $MGSO_4$. After the solvent was removed under vaccum, the residue was separated by column chromatography (eluent: ethyl acetate and petroleum either) to afford 21 mg N-Deacetyl-N-(2,4-dichloro-5-methylphenylthioacetyl)thiocolchicine.

The chemical structure analysis was performed by $^1$HNMR (CDCl$_3$, 600 MHz).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2$=$R_3$=OH, B is methoxy);
N-deacetyl 2,3-dihydroxycolchicine ($R_2$=$R_3$=OH, B is methylthio);
N-deacetyl-3-hydroxycolchicine ($R_2$=$R_3$=methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2$=B=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 26

A. N-Deacetyl-N-(2,3,4,5,6-pentafluorophenoxyacetyl) thiocolchicine (000912)

The reaction mixture of N-deacetylthiocolchicine (15 mg, 0.04 mmol), (2,3,4,5,6-pentafluorophenoxyacetic) acid (19 mg, 0.08 mmol), EDCI (20 mg), DMAP (2 mg, 0.2 mmol) and dichloromethane (3 ml) was stirred at room temperature for 20 h. Then dichloromethane (20 ml) was added. Organic layer was washed with $H_2O$, sat. $NaHCO_3$ and brine, and then dried over $MgSO_4$. After the solvent was removed under vaccum, the residue was separated by column chromatography (eluent: ethyl acetate and petroleum ether) to afford 13 mg N-Deacetyl-N-(2,3,4,5,6-pentafluorophenoxyacetyl)thioclochicine.

The chemical structure analysis was performed by $^1$HNMR (CDCl$_3$, 600 MHz).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2$=$R_3$=OH, B is methoxy);
N-deacetyl 2,3-dihydroxycolchicine ($R_2$=$R_3$=OH, B is methylthio);
N-deacetyl-3-hydroxycolchicine ($R_2$=$R_3$=methoxy, $R_3$ is hydroxy);
N-deacetyl-3-hydroxythiocolchicine ($R_2$ is methoxy, $R_3$ is hydroxy, B is methylthio);

N-deacetyl-3-glucosylcolchicine ($R_2$=B=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 27

N-Deacetyl-N-(1-t-butoxycarbonyl-2-pyrrolidinecarbonyl)thiocolchicine (000915)

The reaction mixture of N-deacetylthiocolchicine (15 mg, 0.04 mmol), 1-t-butoxycarbonyl-2-pyrrolidinoic, acid (17 mg, 0.08 mmol), EDCI (25 mg, 0.13 mmol), DMAP (2 mg, 0.2 mmol) and dichloromethane (3 ml) was stirred at room temperature for 20 h. Then dichloromethane (20 ml) was added. Organic layer was washed with O, 5% $Na_2CO_3$ and brine, and then dried over $MgSO_4$. After the solvent was removed under vaccum, the residue was separated by column chromatography (eluent: ethyl acetate and petroleum ether) to afford 21.4 mg N-Deacetyl-N-(1-t-butoxycarbonyl-2-pyrrocolidinecarbonyl)thioclochicine.

The chemical structure analysis was performed by $^1$HNMR ($CDCl_3$, 600 MHZ).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2$=$R_3$=OH, B is methoxy);
N-deacetyl 2,3-dihydroxycolchicine ($R_2$=$R_3$=OH, B is methylthio);
N-deacetyl-3-hydroxycolchicine ($R_2$=$R_3$=methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2$=B=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 28

N-Deacetyl-N-(3-phthalimidopropionyl)thiocolchicine (000925)

The reaction mixture of N-deactylthiocolchicine (15 mg, 0.04 mmol), 3-phthalimidopropionic acid (175 mg, 0.08 mmol), EDCI (25 mg, 0.13 mmol), DMAP (2 mg, 0.2 mmol) and dichloromethane (3 ml) was stirred at room temperature for 20 h. Then dichloromethane (20 ml) was added. Organic layer was washed with $H_2O$, sat $NaHCO_3$ and brine, and then dried over $MgSO_4$. After the solvent was removed under vaccum, the residue was separated by column chromatography (eluent: ethyl acetate and petroleum ether) to afford 17.6 mg N-Deacetyl-N-(3-phthalimidopropionyl)thioclochicine, mp 138–140° C.

The chemical structure analysis was performed by $^1$HNMR ($CDCl_3$, 600 MHz).

B.

Similarly, by following the procedures of part A of this example but substituting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2$=$R_3$=OH, B is methoxy);
N-deacetyl 2,3-dihydroxycolchicine ($R_2$=$R_3$=OH, B is methylthio);
N-deacetyl-3-hydroxycolchicine ($R_2$=$R_3$=methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2$=B=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 29

A. N-Deacetyl-N-(3-[4-bromobenzoyl]propionyl)thiocolchicine (000926)

The reaction mixture of N-deacetylthiocolchicine (15 mg, 0.04 mmol), 3-(4-bromobenzoyl)-propionic acid (20 mg, 0.08 mmol), EDCI (25 mg, 0.13 mmol), DMAP (2 mg, 0.2 mmol) and dichloromethane (3 ml) was stirred at room temperature for 20 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 21.8 mg N-Deacetyl-N-(3-[4-bromobenzoyl]propionyl)thiocolchicine.

The chemical structure analysis was performed by $^1$HNMR ($CDCl_3$, 600 MHz).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2$=$R_3$=OH, B is methoxy);
N-deacetyl 2,3-dihydroxycolchicine ($R_2$=$R_3$=OH, B is methylthio);
N-deacetyl-3-hydroxyezolchicine ($R_2$=$R_3$=methoxy, $R_3$ is hydroxy);

N-deacetyl-3-hydroxythiocolchicine ($R_2$ is methoxy, $R_3$ is hydroxy, B is methylthio);
N-deacetyl-3-glucosylcolchicine ($R_2$=B=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 30

A. N-Deacetyl-N-(3-fluoro-4-cyanophenoxyacetyl)thiocoichicine (001106)

The reaction mixture of N-deacetylthiocolchicine (15 mg, 0.04 mmol), 3-fluoro-4-cyanophenoxyacetic acid (15.6 mg, 0.08 mmol), EDCI (25 mg, 0.13 mmol), DMAP (2 mg, 0.2 mmol) and dichloromethane (3 ml) was stirred at room temperature for 20 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 17.7 mg N-Deacetyl-N-(3-fluoro-4-cyanophenoxyacetyl)thiocolchicine.

The chemical structure analysis was performed by $^1$HNMR ($CDCl_3$, 600 MHz).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2$=$R_3$=OH, B is methoxy);
N-deacetyl 2,3-dihydroxycolchicine ($R_2$=$R_3$=OH, B is methylthio);
N-deacetyl-3-hydroxycolchicine ($R_2$=$R_3$=methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2$=B=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 31

A. N-Deacetyl-N-(3-trifluoromethyl-4-nitropbenoxyacetyl)thiocolchicine (001107)

The reaction mixture of N-deacetylthiocolchicine (15 mg, 0.04 mmol), 3-trifluoromethyl-4-nitrophenoxyacetic acid (21.6 mg, 0.08 mmol), triethylamine (40 mg, 0.04 mmol) and dichloromethane (5 ml) was stirred at room temperature for 20 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 18 mg N-Deacetyl-N-(3-trifluoromethyl-4-nitrophenoxyacetyl)thiocolchicine, mp 140–142°(dec.).

The chemical structure analysis was performed by $^1$HNMR ($CDCl_3$, 600 MHz).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2$=$R_3$=OH, B is methoxy),
N-deacetyl 2,3-dihydroxycolchicine ($R_2$=$R_3$=OH, B is methylthio);
N-deacetyl-3-hydroxycolchicine ($R_2$=$R_3$=methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2$=B=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 32

A. N-Deacetyl-N-(4-phthalimidobenzoyl)thiocolchicine (001114)

The reaction mixture of N-deacetylthiocolchicine (15 mg, 0.04 mmol), 4-phthalimidobenzoic acid (21 mg, 0.08 mmol), EDCI (25 mg, 0.13 mmol), DMAP (2 mg, 0.2 mmol) and dichloromethane (3 ml) was stirred at room temperature for 20 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 11.6 mg N-Deacetyl-N-(4-phthalimidobenzoyl)thiocolchicine.

The chemical structure analysis was performed by $^1$HNMR ($CDCl_3$, 600 MHz).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2$=$R_3$=OH, B is methoxy);
N-deacetyl 2,3-dihydroxycolchicine ($R_2$=$R_3$=OH, B is methylthio);

N-deacetyl-3-hydroxycolchicine ($R_2=R_3$=methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2$=B=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio), and the like.

EXAMPLE 33

A. N-Deacetyl-N-(3-chloro4-bromophenoxyacetyl) thiocolchicine (001130)

The reaction mixture of N-deacetylthiocolchicine (15 mg, 0.04 mmol), (3-chloro-4-bromophenoxy)acetic acid (20 mg, 0.08 mmol), EDCI (25 mg, 0.13 mmol), DMAP (2 mg, 0.2 mmol) and dichloromethane (3 ml) was stirred at room temperature for 20 h. Then dichloromethane (20 ml) was added. Organic layer was washed with $H_2O$, sat $NaHCO_3$ and brine, and then dried over $MgSO_4$. After the solvent was removed under vaccum, the residue was separated by column chromatography (eluent: ethyl acetate and petroleum ether) to afford 16.4 mg N-Deacetyl-N-(3-chloro-4-bromophenoxyacetyl)thiocolchicine.

The chemical structure analysis was performed by $^1$HNMR ($CDCl_3$, 600 MHz).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2=R_3$=OH, B is methoxy);
N-deacetyl 2,3-dihydroxycolchicine ($R_2=R_3$=OH, B is methylthio);
N-deacetyl-3-hydroxycolchicine ($R_2=R_3$=methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2$=B=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 34

A. N-Deacetyl-N-(4-[3-methoxyphenyl]-piperazinylpropionyl)thiocolchicine (001225)

The reaction mixture of N-deacetylthiocolchicine (15 mg, 0.04 mmol), 4-(3-methoxyphenyl)-piperazinylpropionic acid (15 mg, 0.056 mmol), EDCI (27 mg), DMAP (2 mg, 0.2 mmol) and dichloromethane (3 ml) was stirred at room temperature for 12 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 20 mg N-Deacetyl-N-(4-[3-methoxyphenyl]-piperazinylpropionyl)thiocolchicine, mp 70–72° C.

The chemical structure analysis was performed by $^1$HNMR ($CDCl_3$, 600 MHz).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are mnethylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2=R_3$=OH, B is methoxy);
N-deacetyl 2,3-dihydroxycolchicine ($R_2=R_3$=OH, B is methylthio);
N-deacetyl-3-hydroxycolchicine ($R_2=R_3$=methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2$=B=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 35

A. N-Deacetyl-N-(3-(4-[3-trifluoromethylphenyl]piperazinyl)propionyl)thiocolchicine (001227)

The reaction mixture of N-deacetylthiocolchicine (15 mg, 0.04 mmol), 3-[4-(3-trifluoromethylphenyl)piperazinyl] propionic acid (18 mg, 0.06 mmol), EDCI (27 mg), DMAP (2 mg, 0.2 mmol) and dichloromethane (3 ml) was stirred at room temperature for 20 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 18.4 mg N-Deacetyl-N-(3-(4-[3-trifluoromethylphenyl]piperazinyl)propionyl) thiocolchicine.

The chemical structure analysis was performed by $^1$HNMR ($CDCl_3$, 600 MHz).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methyl methoxy, B-is methythio);
N-deacetyl-2,3dihydroxycolchicine ($R_2=R_3$=OH, B is methoxy);

N-deacetyl 2,3-dihydroxycolchicine ($R_2=R_3=OH$, B is methylthio);
N-deacetyl-3-hydroxycolchicine ($R_2=R_3$=methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2$=B=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 36

A. N-Deacetyl-N-(2,6-diiodo-4-cyanophenoxyacetyl) thiocolchicine (001229)

The reaction mixture of N-deacetylthiocolchicine (15 mg. 0.04 mmol), 2,6-diiodo-4-cyanophenoxyacetic acid (25 mg, 0.06 mmol), EDCI (25 mg, 0.13 mmol), DMAP (2 mg, 0.2 mmol) and dichloromethane (3 ml) was stirred at room temperature for 20 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 21.4 mg N-Deacetyl-N-(2,6-diiodo-4-cyanophenoxyacetyl)thiocolchicine.

The chemical structure analysis was performed by $^1$HNMR ($CDCl_3$, 600 MHz).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2=R_3=OH$, B is methoxy);
N-deacetyl 2,3-dihydroxycolchicine ($R_2=R_3=OH$, B is methylthio);
N-deacetyl-3-hydroxycolchicine ($R_2=R_3$=methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2$=B=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 37

A. N-Deacetyl-N-4-[2-phenyl]quinolinecarbonyl) thiocolchicine (001213).

The reaction mixture of N-deacetylthiocolchicine (15 mg., 0.04 mmol), 4-(2-phenyl)quinolinecarboxylic acid (23 mg), EDCI (21 mg), DMAP (2 mg, 0.02 mmol) and dichloromethane (3 ml) was stirred at room temperature until reaction was complete. Then dichloromethane (20 ml) was added. Organic layer was washed with $H_2O$, sat $NaHCO_3$ and brine, and then dried over $MgSO_4$. After the solvent was removed under vaccum, the residue was separated by column chromatography (eluent: ethyl acetate and petroleum ether) to afford 17.9 mg N-Deacetyl-N-(4-[2-phenyl] quinolinecarbonyl)thiocolchicine.

The chemical structure analysis was performed by $^1$HNMR ($CDCl_3$, 600 MHz).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2=R_3=OH$, B is methoxy);
N-deacetyl 2,3-dihydroxycolchicine ($R_2=R_3=OH$, B is methylthio);
N-deacetyl-3-hydroxycolchicine ($R_2=R_3$=methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2$=B=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 38

A. N-Deacetyl-N-(phenothiazin-10-ylcarbonyl) thiocolchicine (000928).

The reaction mixture of N-deacetylthiocolchicine (15 mg, 0.04 mmol), phenothiazin-10-ylcarbonylchloride (12 mg, 0.045 mmol), DMAP (4 mg, 0.02 mmol) and dichloromethane (3 ml) was stirred at room temperature for 48 h. Then dichloromethane (20 ml) was added. Organic layer was washed with $H_2O$, sat. $NaHCO_3$ and brine, and then dried over $MgSO_4$. After the solvent was removed under vaccum, the residue was separated by column chromatography (eluent: ethyl acetate and petroleum ether) to afford 12 mg N-Deacetyl-N-(phenothiazin-10-ylcarbonyl) thiocolchicine.

The chemical structure analysis was performed by $^1$HNMR ($CDCl_3$, 600 MHz).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);

N-deacetyl-2,3-dihydroxycolchicine ($R_2=R_3$=OH, B is methoxy);
N-deacetyl 2,3-dihydroxycolchicine ($R_2=R_3$=OH, B is methylthio);
N-deacetyl-3-hydroxycolchicine ($R_2=R_3$=methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2$=B=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 39

A. N-Deacetyl-N-(1,7-dimethylnaphthyridin-4-one-3-carboxy)thiocolchicine (000920).

The reaction mixture of N-deacetylthiocolchicine (24 mg, 0.06 mmol), 1,7-dimethyl-naphthyridin-4-one-3-carboxylic acid (25 mg. 0.13 mmol), EDCI (29 mg. 0.13 mmol), DMAP (2 mg, 0.02 mmol) and dichloromethane (3 ml) was stirred at room temperature for 20 h. Then dichloromethane (20 ml) was added. Organic layer was washed with $H_2O$, 5% $Na_2CO_3$ and brine, and then dried over $MgSO_4$. After the solvent was removed under vaccum, the residue was separated by column chromatography (eluent: ethyl acetate and petroleum ether) to afford 24.3 mg N-Deacetyl-N-(1,7-dimethylnaphthyridin-4-one-3-carboxy)thiocolchicine.

The chemical structure analysis was performed by $^1$HNMR ($CDCl_3$, 600 MHz).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2=R_3$=OH, B is methoxy);
N-deacetyl 2,3-dihydroxycolchicine ($R_2=R_3$=OH, B is methylthio);
N-deacetyl-3-hydroxycolchicine ($R_2=R_3$=methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2$=B=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 40

This example provides directions for growing cells and testing compounds of the invention for their effect on the growth of the cells. All cells were purchased from DCTDC Tumor Repository, NCI, NIH.

Cell Colony Formation Assay

Four hundred cells (HCT 116, PC-3) or five hundred cells (VM46) were plated in 60 mm Petri dishes containing 2.7 ml of medium (modified McCoy's 5a medium) containing 10% fetal bovine serum and 100 units/ml penicillin and 100 mg/ml streptomycin. The cells were incubated in a $CO_2$ incubator at 37° C. for 5 hours for attachment to the bottom of Petri dishes. Drugs were made fresh in medium at ten times the final concentration, and then 0.3 ml of this stock solution was added to the 2.7 ml of medium in the dish. The cells were then incubated with drugs for 72 hours at 37° C. At the end of the incubation the drug-containing media were decanted, the dishes were rinsed with 4 ml of Hank's Balance Salt Solution (HBSS), 5 ml of fresh medium was added, and the dishes were returned to the incubator for colony formation. The cell colonies were counted using colony counter after incubation for 7 days for HCT116 cells and PC-3 cells and 8 days for VM46 cells, respectively. Cell survival (%) was calculated, as shown in Table I for HCT 116 cells.

Values of ID50 (the drug concentration producing 50% inhibition of colony formation) may be determined for each tested compound. The directions described in this example may be used in other cells, such as DU-145.

TABLE I

This table provides results of in vitro efficacy tests performed in example 22 for the cell line HCT116.

| Compound | Survival (%) of HCT116 | | |
|---|---|---|---|
| (Example #) | 100 nM | 10 nM | 1 nM |
| Colchicine | 0 | 76.1 | 100 |
| Thiocolchicine | 0 | 0 | 100 |
| N-Deacctylthiocolchicine | 0 | 89.7 | 100 |
| 000811 | 0 | 50.4 | |
| 000814 | 0 | 87.7 | |
| 000815 | 0 | 93.8 | |
| 000816 | 0 | 100 | |
| 000817 | 0 | 99.8 | |
| 000818 | 0 | 98.8 | |
| 000825 | 0 | 0 | 90.25 |
| 000829 | 0 | 0 | 100 |
| 000901 | 0 | 61.60 | |
| 000831 | 89.15 | | |
| 000830 | 0 | 9.01 | |
| 000905 | 96.66 | | |
| 000909 | 92.31 | | |
| 000906 | 0 | 0 | 98.67 |
| 000911 | 0 | 0 | 100 |
| 000828 | 93.81 | | |
| 000908 | 0 | 100 | |
| 000912 | 0.50 | 100 | |
| 000913 | 1.00 | 90.91 | |
| 000914 | 0 | 3.54 | |
| 000915 | 70.12 | | |
| 000918 | 13.61 | | |
| 000920 | 95.68 | | |
| 000921 | 0 | 96.18 | |
| 000922 | 0 | 0 | 100 |
| 000925 | 0 | 98.67 | |
| 000926 | 0 | 100 | |
| 000927 | 0 | 100 | |
| 000928 | 100 | | |
| 001024 | 0 | 98.0 | |
| 001106 | 0 | 98.51 | |
| 001107 | 100 | | |
| 001114 | 95.05 | | |
| 001127 | 0 | 75.37 | |
| 001201 | 95.07 | | |
| 001207 | 3.10 | | |
| 001213 | 62.56 | | |
| 001225 | 0 | 80.5 | |

TABLE I-continued

This table provides results of in vitro efficacy tests performed in example 22 for the cell line HCT116.

| Compound | Survival (%) of HCT116 | | |
|---|---|---|---|
| (Example #) | 100 nM | 10 nM | 1 nM |
| 001227 | 0 | 100 | |
| 001229 | 0 | 100 | |

EXAMPLE 41

This example provides directions for performing in vivo toxicity tests of the compounds of the invention on C3H/HeJ mice.

Acute toxicities of the compounds of this invention are evaluated on C3H/HeJ mice (body weight 18–22 g). The MTD40 (maximum tolerated dose at day 40) values are determined by the standard procedure described by Gad and Chengelis (see, for example, "Acute Toxicology Testing," $2^{nd}$ Ed., Shayne O. Gad and Christopher P. Chengelis, pp. 186–195 (Academic Press).) In the consecutive type studies, 2 mice are dosed at low and moderate doses of 40 and 100 mg/kg. If no severe and irreversible toxicity (euthanasia is required) occurs at these doses, a new pair of animals is initiated at 180 mg/kg, which is 1.8 times higher than 100 mg/kg. Sequential dosages (about 3 doses on 3 pairs of animals, i.e. 2 mice for each drug dose) are increased by a factor of 1.8 until severe and irreversible toxicity (euthanasia is required) occurred. Then another pair of animals is initiated at the highest nonlethal dosage, and successive dosages were increased by a factor of 1.15. The result of this exercise is two dosages, one apparently nonlethal and the other lethal if severe and irreversible toxicity occurs and euthanasia is required, separated by a factor of 1.15. Six mice are dosed at each dosage. If no severe and irreversible toxicity occurs at the lower dosage and at least one with severe and irreversible toxicity occurs at the higher dose, then the lower dose is considered to be the MTD. The compounds of this invention are administered to C3H/HeJ mice by intraperitoneal injection (IP). Drug toxicity is evaluated on mice checked daily for 45 days. The toxicity parameters reported will be the MTD40. The MTD or nontoxicity dose (mg/kg) is defined as the highest dose causing no severe irreversible toxicity in one treatment group, but at least one animal exhibiting severe and irreversible toxicity and being euthanized at the next higher dose.

EXAMPLE 42

This example provides directions for performing in vivo efficacy tests of the compounds of the invention on C3H/HeJ mice bearing MTG-B tumors.

Studies on the compounds of this invention are performed on C3H/HeJ mice bearing MTG-B tumors. The tumors grow exponentially following implantation into the flanks of the mice and reached a diameter of 8 mm (268.08 mm$^3$) by day 7 to 10. Treatment is initiated at that time, with the first day of treatment designated as day 0 for calculation and plots. The mice are injected i.p. with three drug dose levels (⅓, ½, 1 5 MTD) using both a single injection and the schedule of Q2D 5 3 (every 2 days for a total of 3 treatments at ⅓ MTD). Control groups of mice bearing 8 mm diameter tumors are treated with vehicle alone. After drug treatment, the mice are observed twice a day. When a tumor reaches 1.5 g, the mouse bearing the tumor wis euthanized. Surviving days measured from day 0 for mice treated with anticancer drugs (T) and surviving days measured from day 0 for control mice (C) are recorded. Tumor growth inhibition values (T/C %) are calculated using the formula T/C %=(surviving days of mice treated with an anticancer drug T/surviving days of control mice C) 5 100%.

Tumor sizes may be measured by caliper every day. Daily measurement (mm) of solid tumor (length L and width W) in two dimensions is used to calculate the tumor weight [tumor weight=(length 5 width$^2$)/2] based on the interchangeable value of 1 mm$^3$=1 mg. Tumor growth delay (T–C value) is determined by calculation of the median time (in days) required for the treatment group and control group tumors to reach 1,000 mg. Tumor doubling time (Td) is measured, and tumor cell kill is calculated by the formula of log cell kill=(T–C value)/(3.32 5 Td). Regression effects after treatment may be observed and recorded (a complete regression: a regression below limit of palpation; a partial regression: a regression of more than 50% reduction in tumor mass).

Generally, the survival time of the control mice is six (6) days. A ratio of the extra days of survival of mice treated with the compounds of the invention (compared to control) to the extra days of survival of mice treated with taxol (compared to control), can be calculated. For example, if the mice survived 18 days as compared to 9 days for taxol-treated mice, the CD/Taxol ratio would be 18–6/9–6=12/3=4 or 400%.

The following Table II provides a summary of the in vivo toxicity and iv vivo efficacy tests described in Examples 41 and 42 for the compounds tested.

TABLE II

| | | Invivo Efficacy | |
|---|---|---|---|
| Compound | In Vivo Toxicity Nontoxicity Dose (ip. mg/kg) in C₃H/Hej mice | Surviving days after treatment of MTG-B mouse mammary adenocarcinoma in C₃H/Hcj mice | T/C % |
| Colchicine | 1.6 (0.5) | 9 | 150 |
| Thiocolchicine | 1.0 | | |
| N-Deacctylthiocolchicine | | | |
| 000811 | 150 | | |
| 000814 | 100 | | |
| 000815 | 100 (100) | 9 | 150 |
| 000816 | 100 | | |
| 000817 | 100 | | |
| 000818 | 100 (70) | 8 | |
| 000825 | 50 (30) | 18 | |
| 000829 | 150 (120) | 13 | 217 |
| 000830 | 150 (120) | 8 | 133 |
| 000906 | 50 | | |
| 000911 | 30 (30) | 11 | 183 |
| 000914 | 150 (120) | | |

EXAMPLE 43

This example provides guidance for determining the inhibition of topoisomerase I. This procedure is an intact cell assay and is a modification of a published procedure found at *Cancer Res.* 1986, 46, 2021–2026. A more recent publication can be found at *J. Med. Chem.* 1993, 36 2689–2700 at 2699. Here the modification of the previous procedure was used to quantitate the amount of topoisomerase I mediated DNA cleavage in intact cells. The DNA of HL-60 cells growing in culture is labeled by [$^3$H]thymidine incorporation. The cells are exposed to compounds to be tested and lysed, and the protein is precipitated. Radioactive DNA in cleavable complex formation with topoisomerase I coprecipitates with the protein. The amount of cleavable complex formation is quantitated by counting the pellet with a liquid scintillation counter.

EXAMPLE 44

A. Dimer of N-Deacetylthiocolchicine (000927)

This example teaches how to make a dimer of N-deacetylthiocolchicine using a diacid. The reaction mixture of N-deacetylthiocolchicine (15 mg, 0.04 mmol), 4-carboxyphenoxyacetic acid (4.0 mg, 0.02 mmol), EDCI (20 mg), DMAP (2 mg, 0.2 mmol), DMF (2 ml) and dichloromethane (2 ml) was stirred at room temperature for 20 h. Then dichloromethane (20 ml) was added. Organic layer was washed with $H_2O$, sat. $NaHCO_3$ and brine, and then dried over $MgSO_4$. After the solvent was removed under vaccum, the residue was separated by column chromatography (eluent: ethyl acetate and petroleum ether) to afford the dimer of N-deacetylthiocolchicine, i.e., the diamide of the 4-carboxyphenoxyacetic acid.

The chemical structure analysis was performed by $^1$HNMR ($CDCl_3$, 600 MHz).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2=R_3=OH$, B is methoxy);
N-deacetyl 2,3-dihydroxycolchicine ($R_2=R_3=OH$, B is methylthio);
N-deacetyl-3-hydroxycolchicine ($R_2=R_3$=methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2=B$=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

EXAMPLE 45

A. Dimer of N-Deacetylthiocolchicine (000828)

This example teaches how to make another dimer of N-deacetylthiocolchicine using a diacid. The reaction mixture of N-deacetylthiocolchicine (20 mg, 0.0536 mmol), 3,4-di-(4-carboxymethoxyphenyl)-3,4-hexene (10 mg, 0.026 mmol), EDCI (25 mg) DMAP (2 mg, 0.2 mmol) and dichloromethane (3 ml) was stirred at room temperature for 20 h. Then dichloromethane (20 ml) was added. Organic layer was washed with $H_2O$, 5% $Na_2CO_3$ and brine, and then dried over $MgSO_4$. After the solvent was removed under vacuum, the residue was separated by column chromatography (eluent: ethyl acetate and petroleum ether) to afford 15 mg of the dimer of N-deacetylthiocolchicine, i.e. the diamide of 3,4-di-(4-carboxymethoxyphenyl)-3,4-hexene.

The chemical structure analysis was performed by $^1$HNMR ($CDCl_3$, 600 MHz).

B.

Similarly, by following the procedures of part A of this example but substitutting other N-deacetylthiocolchicines or N-deacetylcolchicines listed below for N-deacetylthiocolchicine, other similar compounds of this invention are obtained:

N-deacetylcolchicine;
N-deacetylthiocolchicine;
N-deacetyl-2,3-methylenedioxycolchicine ($R_2$ and $R_3$ together are methylenedioxy, B is methoxy);
N-deacetyl 2,3-methylenedioxythiocolchicine ($R_2$ and $R_3$ together are methylenedioxy, B-is methythio);
N-deacetyl-2,3-dihydroxycolchicine ($R_2=R_3=OH$, B is methoxy);
N-deacetyl 2,3-dihydroxycolchicine ($R_2=R_3=OH$, B is methylthio);
N-deacetyl-3-hydroxycolchicine ($R_2=R_3$ methoxy, $R_3$ is hydroxy);
N-deacetyl-3-hydroxythiocolchicine ($R_2$ is methoxy, $R_3$ is hydroxy, B is methylthio);
N-deacetyl-3-glucosylcolchicine ($R_2=B$=methoxy $R_3$ is glucosyl);
N-deacetyl-3-glucosylthiocolchicine ($R_2$ is methoxy, $R_3$ is glucosyl, B is methylthio);
N-deacetyl-3-galactosidylcolichicine ($R_2$ is methoxy, $R_3$ is galactosidyl, B is methoxy);
N-deacetyl-3-galactosidylthiocolchicine ($R_2$ is methoxy, $R_3$ is galactosidyl, B is methylthio); and the like.

What is claimed is:

1. A compound represented by the formula

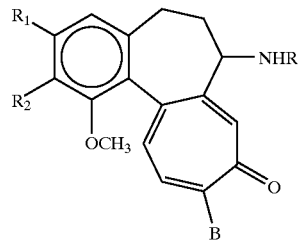

wherein
R is C(O)—(CHR$_4$)$_m$—A—R$_1$ where
m is 1–10,
A is S, O, N or a covalent bond,
R$_1$ is
substituted phenyl, wherein the phenyl is substituted with from one to five substituents independently selected from the group consisting of halo, lower alkyl of 1–6 carbons, hydroxy, lower alkoxy of 1–6 carbons, cyano, nitro, amino, halogenated lower alkyl of 1–6 carbons, halogenated lower alkoxy of 1–6 carbons, carbonyl, hydroxycarbonyl, lower alkylcarbonyloxy of 1–6 carbons, benzyloxy; optionally substituted 5 membered heterocyclic ring optionally substituted with one or two substituents selected from the group consisting of halo, lower alkyl of 1–6 carbons, lower alkoxy of 1–6 carbons, hydroxy, cyano, nitro, amino, halogenated lower alkyl of 1–6 carbons, halogenated lower alkoxy of 1–6 carbons, hydroxycarbonyl, lower alkoxycarbonyl of 1–6 carbons, lower alkylcarbonyloxy of 1–6 carbons, and lower alkylcarbonylamino of 1–6 carbons; optionally substituted 6 membered heterocyclic ring optionally substituted with one or two substituents selected from the group consisting of halo, lower alkyl of 1–6 carbons, lower alkoxy of 1–6 carbons, hydroxy, cyano, nitro, amino, halogenated lower alkyl of 1–6 carbons, halogenated lower alkoxy of 1–6 carbons, hydroxycarbonyl, lower alkoxycarbonyl of 1–6 carbons, lower alkylcarbonyloxy of 1–6 carbons, lower alkylcarbonylamino of 1–6 carbons, or optionally substituted phenyl or benzyl; an imide ring, lower alkoxycarbonyl of 1–6 carbons, and lower alkylcarbonylamino of 1–6 carbons, or substituted benzoyl, wherein the benzoyl is substituted with from one to five substituents independently selected from the group consisting of halo, lower alkyl of 1–6 carbons, hydroxy, lower alkoxy of 1–6 carbons, cyano, nitro, amino, halogenated lower alkyl of 1–6 carbons, halogenated lower alkoxy of 1–6 carbons, carbonyl, hydroxycarbonyl, lower alkylcarbonyloxy of 1–6 carbons, benzyloxy, optionally substituted 5 membered heterocyclic ring, optionally substituted 6 membered heterocyclic ring, an imide ring, lower alkoxycarbonyl of 1–6 carbons, and lower alkylcarbonylamino of 1–6 carbons;

B is methoxy or methylthio,

R2 is methoxy, hydroxy, or methylenedioxy when taken together with R3; and

R3 is methoxy, hydroxy, a monosaccharide radical, or is methylenedioxy when taken together with R2; and m is H or is H or methyl when m is 1.

2. The compound of claim 1, wherein R4 is hydrogen and R1 is phenyl substituted with one to five substituents independently selected from the groups consisting of halo, lower alkyl of 1–6 carbons, hydroxy, lower alkoxy of 1–6 carbons, cyano, nitro, amino, halogenated lower alkyl of 1–6 carbons, halogenated lower alkoxy of 1–6 carbons, carbonyl, hydroxycarbonyl, lower alkylcarbonyloxy of 1–6 carbons, benzyloxy, optionally substituted 5 or 6 membered heterocyclic ring, an imide ring, lower alkoxycarbonyl of 1–6 carbons, and lower alkylcarbonylamino of 1–6 carbons.

3. The compound of claim 2, wherein $R_2$ is methoxy, $R_3$ is a monsaccharide radical chosen from glucosyl and galactosidyl, and B is methylthio.

4. The compound of claim 2, wherein B is methylthio, $R_2$ is hydroxy or methoxy, and $R_3$ is hydroxy or methoxy.

5. The compound of claim 4, wherein $R_2$ and $R_3$ each is methoxy.

6. The compound of claim 5, wherein m is 1 or 2 and A is S or O.

7. The compound of claim 6, wherein m is 1, A is O, and $R_1$ is 2,3,4,5,6-pentafluorophenyl.

8. The compound of claim 6, wherein m is 1 and $R_1$ is phenyl substituted with 1, 2, or 3 substituents chosen from, halo, methyl, methoxy, $NO_2$, trifluoromethyl, cyano, and an imide ring.

9. The compound of claim 8, wherein $R_1$ is phenyl substituted with one or two halo substituents.

10. The compound of claim 9, wherein A is O.

11. The compound of claim 8, wherein $R_1$ is phenyl substituted with 1 or 2 methyl substituents.

12. The compound of claim 8, wherein $R_1$ is phenyl substituted with 1 or 2 methoxy substituents.

13. The compound of claim 1, wherein $R_1$ is benzoyl substituted with a halo, m is 1 or 2, B is methylthio, and A is a covalent bond.

14. The compound of claim 1 in combination with a pharmaceutically-acceptable excipient to form a pharmaceutical composition.

15. The pharmaceutical composition of claim 13, which is in the form of a liposomal composition.

16. A method for treating cancer in a patient, which method comprises administering a therapeutically effective amount of a compound of claim 1 to the patient.

17. A compound represented by the formula

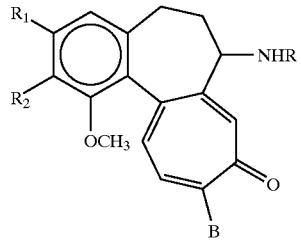

wherein

R is $C(O)-(CHR_4)_m-A-R_1$ where m is 0–10,

A is oxygen, sulfur, nitrogen, or a covalent bond, $R_1$ is selected from the group consisting of
phenyl substituted with one to five substituents selected from an imide ring, and lower alkylcarbonylamino of 1–6 carbons;
optionally substituted cycloalkyl of 3–7 carbons;
optionally substituted naphthyl;
an imide ring;
an optionally substituted 5 or 6 member heterocycle with at least one N in the ring, wherein the 5-membered heterocycle is optionally substituted with one or two substituents selected from the group consisting of halo, lower alkyl of 1–6 carbons, lower alkoxy of 1–6 carbons, hydroxy, cyano, nitro, amino, halogenated lower alkyl of 1–6 carbons halogenated lower alkoxy of 1–6 carbons, hydroxycarbonyl, lower alkoxycarbonyl of 1–6 carbons, lower alkylcarbonyloxy of 1–6 carbons, and lower alkylcarbonylnmino of 1–6 carbons; and wherein the 6 membered heterocycle is optionally substituted with one or two substituents selected from the group consisting of halo, lower alkyl of 1–6 carbons, lower alkoxy of 1–6 carbons, hydroxy, cyano, nitro, amino, halogenated lower alkyl of 1–6 carbons, halogenated lower alkoxy of 1–6 carbons, hydroxycarbonyl, lower alkoxycarbonyl of 1–6 carbons, lower alkylcarbonyloxy of 1–6 carbons, lower alkylcarbonylamino of 1–6 carbons, or optionally-substituted phenyl or benzyl; an optionally substituted furan-2-yl, wherein the furan-2-yl is optionally substituted with one or two substituents selected from the group consisting of halo, lower alkyl of 1–6 carbons, lower alkoxy of 1–6 carbons, hydroxy, cyano, nitro, amino, halogenated lower alkyl of 1–6 carbons, halogenated lower alkoxy of 1–6 carbons, hydroxycarbonyl, lower alkoxycarbonyl of 1–6 carbons, lower alkylcarbonyloxy of 1–6 carbons, and lower alkylcarbonylamino of 1–6 carbons; and an optionally substituted fused heterocyclic or fused carbocyclic ring system, wherein the fused heterocyclic ring system has no more than 2 substituents independently substituted with lower alkyl of 1–6 carbons, lower cycloalkyl of 1–6 carbons, alkoxy, hydroxy, halo, cyano, hydroxy lower alkyl of 1–6 carbons, phenyl wherein the phenyl is unsubstituted or is substituted with from one to five substituents independently selected from the group consisting of halo, lower alkyl of 1–6 carbons, hydroxy, lower alkoxy of 1–6 carbons, cyano, nitro, amino, halogenated lower alkyl of 1–6 carbons, halogenated lower alkoxy of 1–6 carbons, carbonyl, hydroxycarbonyl, lower alkylcarbonyloxy of 1–6 carbons, benzyloxy, optionally substituted 5 membered heterocyclic ring, optionally substituted 6 membered heterocyclic ring, an imide ring, lower alkoxycarbonyl of 1–6 carbons, and lower alkylcarbonyhmino of 1–6 carbons; benzyl wherein the benzyl is unsubstituted or is substituted with from one to five substituents independently selected from the group consisting of halo, lower alkyl of 1–6 carbons, hydroxy, lower alkoxy of 1–6 carbons, cyano, nitro, amino, halogenated lower alkyl of 1–6 carbons, halogenated lower alkoxy of 1–6 carbons, carbonyl, hydroxycarbonyl, lower alkylcarbonyloxy of 1–6 carbons, benzyloxy, optionally substituted 5 membered heterocyclic ring, optionally substituted 6 membered heterocyclic ring, an imide ring, lower alkoxycarbonyl of 1–6 carbons, and lower alkylcarbonylamino of 1–6 carbons; aminocarbonylmethyl, lower alkylaminocarbonylmethyl, amino, mono- or di-lower alkylamino, cyclic amino, or a 5- or 6-membered heterocyclic ring;

B is methoxy or methylthio;

R2 is methoxy, hydroxy, or methylenedioxy when taken together with R3;

R3 is methoxy, hydroxy, a monosaccharide radical, or is methylenedioxy when taken together with R2; and m is H or H or methyl when m is 1.

18. The compound of claim 17, wherein B is methylthio, $R_4$ is H, $R_2$ and $R_3$ each is methoxy; m is 0, 1 or 2; and A is oxygen, sulfur, or a covalent bond.

19. The compound of claim 18, wherein $R_1$ is an optionally substituted 5-membered heterocycle with one, two, or three nitrogens in the ring.

20. The compound of claim 19, wherein $R_1$ is 1H-tetrazol-1-yl, 1-t-butoxycarbonyl-pyrrolidin-2-yl.

21. The compound of claim 18, wherein m is 0, A is a covalent bond, and $R_1$ is optionally substituted furan-2-yl.

22. The compound of claim 21, wherein $R_1$ is 5-nitrofuran-2-yl.

23. The compound of claim 18, wherein A is O.

24. The compound of claim 18, wherein m is 0, A is a covalent bond, and $R_1$ is phenyl substituted with an imide ring or alkyl-carbonylamino.

25. The compound of claim 24, wherein $R_1$ is 4-phthalimidophenyl or 3-chloroacetylaminophenyl.

26. The compound of claim 18, wherein $R_1$ is an optionally substituted 6-membered heterocycle with one or two nitrogens in the ring.

27. The compound of claim 26, wherein A is a covalent bond and the 6-membered heterocycle is pyridine-3-yl, thymin-1-yl, or piperazin-1-yl.

28. The compound of claim 27, wherein $R_1$ is pyridin-3-yl, thymin-1-yl, 4-(3-methoxyphenyl)piperazin-1-yl, or 4-(3-trifluoromethylphenyl)piperazin-1-yl.

29. The compound of claim 18, wherein A is a covalent bond and $R_1$ is an imide ring.

30. The compound of claim 29, wherein $R_1$ is phthalimido.

31. The compound of claim 18, wherein $R_1$ is a fused heterocyclic ring system.

32. The compound of claim 31, wherein m is O, A is a covalent bond, and $R_1$ is optionally substituted quinolin-4-yl, optionally substituted phenothiazin-10-yl, or optionally substituted naphthyrid-4-on-3-yl.

33. The compound of claim 32, wherein $R_1$ is 2-phenylquinolin-4-yl, phenothiazin-10-yl, or 1,7-dimethyl-naphthyridin-4-on-3-yl.

34. The compound of claim 31, wherein the fused heterocyclic ring system is chromon-2-yl.

35. The compound of claim 34, wherein m is O and A is a covalent bond.

36. The compound of claim 18, wherein $R_1$ is a fused carbocyclic system.

37. The compound of claim 36, wherein m is O, A is a covalent bond $R_1$ is anthraquinon-1-yl.

38. The compound of claim 36, wherein m is 1, A is oxygen and $R_1$ is 2,3,4,7-tetranitro-9-fluorenylideneamino.

39. The compound of claim 18, wherein m is 1, A is oxygen, an $R_1$ is quinolin-4-yl.

40. The compound of claim 17 in combination with a pharmaceutically-acceptable excipient to form a pharmaceutical composition.

41. The pharmaceutical composition of claim 40 which is in the form of a liposomal formulation.

42. A method for treating cancer in a patient, which method comprises administering a therapeutically effective amount of a compound of claim 17 to the patient.

43. A compound represented by the formula

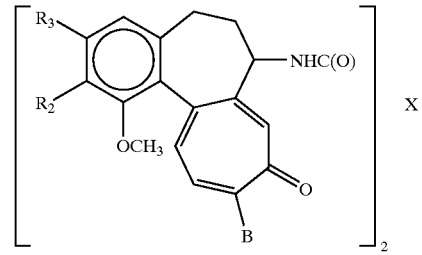

wherein

B is methoxy or methylthio;

$R_2$ is methoxy, hydroxy, or methylenedioxy when taken together with $R_3$;

$R_3$ is methoxy, hydroxy, a monosaccharide radical, or is methylenedioxy when taken together with $R_2$; and X is 4-phenoxymethyl or 3,4-di(methoxyphenyl)-3,4-hexene.

44. The compound of claim 43, wherein $R_2$ and $R_3$ each is methoxy.

45. The compound of claim 44, wherein B is methylthio and X is 4-phenoxymethyl.

46. The compound of claim 44, wherein B is methylthio and X is 3,4-di(methoxyphenyl)-3,4-hexene.

47. The compound of claim 43 in combination with a pharmaceutically-acceptable excipient to form a pharmaceutical composition.

48. The pharmaceutical composition of claim 47, which is in the form of a liposomal composition.

49. A method for treating cancer in a patient, which method comprises administering a therapeutically effective amount of a compound of claim 43 to the patient.

* * * * *

UNITED STATES PATENT AND TRADEMARK OFFICE
CERTIFICATE OF CORRECTION

PATENT NO.        : 6,825,236 B2                                          Page 1 of 2
APPLICATION NO. : 10/414076
DATED                : November 30, 2004
INVENTOR(S)       : Li-Xi Yang It is certified that error appears in the above-identified patent and that said Letters Patent is hereby corrected as shown below:

Column 50, Claim 1

Line 35, " 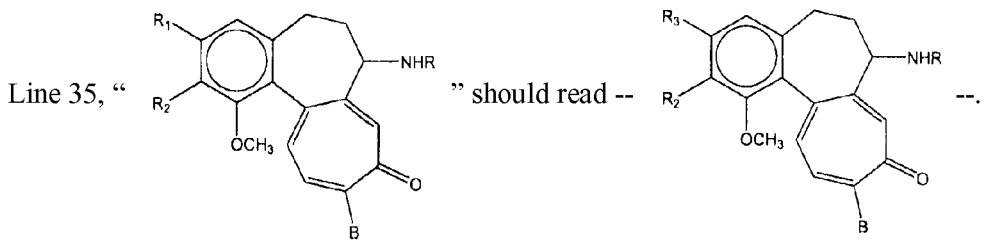 " should read -- --.

Line 49, "A is S, O, N" should read -- A is S, O, NH --.

Column 51

Line 25, "R2 is" should read -- $R_2$ is --.

Line 26, "together with R3" should read -- together with $R_3$ --.

Line 27, "R3 is" should read -- $R_3$ is --.

Line 28, "R2 is" should read -- $R_2$ is --.

Line 29, "m is H" should read -- $R_4$ is H --.

Column 51, Claim 2

Line 30, "R4 is" should read -- $R_4$ is --.

Line 31, "R1 is" should read -- $R_1$ is --.

Column 52, Claim 17

Line 7, 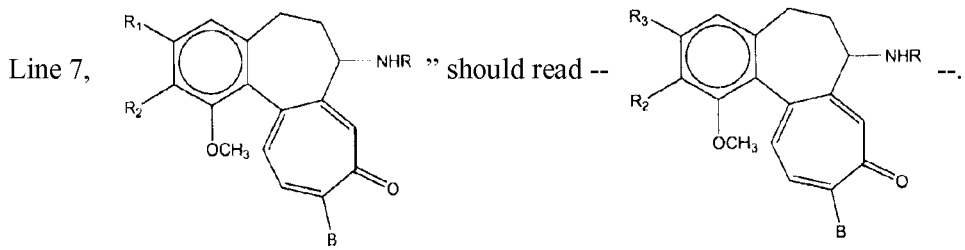 " should read -- --.

UNITED STATES PATENT AND TRADEMARK OFFICE
CERTIFICATE OF CORRECTION

PATENT NO.       : 6,825,236 B2
APPLICATION NO.  : 10/414076
DATED            : November 30, 2004
INVENTOR(S)      : Li-Xi Yang It is certified that error appears in the above-identified patent and that said Letters Patent is hereby corrected as shown below:

Line 22, "nitrogen" should read -- NH --.

Column 53

Line 28, "R2 is" should read -- $R_2$ is --.

Line 29, "together with R3" should read -- together with $R_3$ --.

Line 30, "R3 is" should read -- $R_3$ is --.

Line 31, "R2 is" should read -- $R_2$ is --.

Line 32, "m is H" should read -- $R_4$ is H --.

Signed and Sealed this

Thirtieth Day of September, 2008

JON W. DUDAS
*Director of the United States Patent and Trademark Office*